(12) United States Patent
Jensen

(10) Patent No.: US 7,265,209 B2
(45) Date of Patent: Sep. 4, 2007

(54) CE7-SPECIFIC CHIMERIC T CELL RECEPTOR

(75) Inventor: Michael Jensen, Pasadena, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/477,572

(22) Filed: Jun. 30, 2006

(65) Prior Publication Data

US 2006/0246548 A1  Nov. 2, 2006

Related U.S. Application Data

(62) Division of application No. 10/120,198, filed on Apr. 11, 2002, now Pat. No. 7,070,995.

(60) Provisional application No. 60/282,859, filed on Apr. 11, 2001.

(51) Int. Cl.
*C12P 21/08* (2006.01)
*C07K 16/00* (2006.01)
*C12N 5/06* (2006.01)
*C12N 5/08* (2006.01)
*C12P 21/04* (2006.01)
*A61K 39/395* (2006.01)

(52) U.S. Cl. ............................. 530/387.3; 530/388.22; 530/388.8; 530/388.85; 435/328; 435/344.1; 435/372; 435/372.3; 424/134.1; 424/135.1; 424/143.1; 424/155.1

(58) Field of Classification Search ............ 530/387.3, 530/388.3, 388.85; 435/372.3, 325, 328, 435/344, 344.1
See application file for complete search history.

(56) References Cited

U.S. PATENT DOCUMENTS 5,912,172 A * 6/1999 Eshhar et al.
6,410,319 B1  6/2002 Raubitschek et al.

FOREIGN PATENT DOCUMENTS

WO   WO9715669 A1 * 5/1997
WO   WO 00/23573 A2   4/2000
WO   WO 00/31239 A1   6/2000

OTHER PUBLICATIONS

Nolan et al. Clinical Cancer Research, 5(12):3928-3941, 1999.*
Gonzalez et al. Journal of Genetic Medicine, 6(6):704-711, 2004.*
Hombach et al. Int. J. Mol. Med., 2(1):99-103, 1998.*
Sadelain et al. Nature Reviews, 3:35-45, 2003.*
Jensen, M et al. "CD20 Is A Molecular Target For scFvFc:ζ Receptor Redirected T Cells: Implications For Cellular Immunotherapy of CD2+ Malignancy," *Biology of Blood and Marrow Transplantation*, 4:75-83, 1998.
Abken, H. et al. "Chimeric T-Cell Receptors: Highly Specific Tools To Target Cytotoxic T-Lymphocytes To Tumour Cells," *Cancer Treatment Reviews*, 23:97-112, 1997.
Nicholson, Ian C. et al. "Construction And Characterisation Of A Functional CD19 Specific Single Chain Fv Fragment . . . ," *Molecular Immunology*, vol. 34, No. 16-17, 1157-1165, 1997.
Jensen, M. C. et al. Abstract #98: "Targeting Pre-B Acute Lymphoblastic Leukemia With T Cell Clones Engineered To Express A CD19-Specific Chimeric Immunoreceptor," Blood, 96(11), p. 26A, Nov. 16, 2000.
Amstutz, H. et al. "Production And Characterization Of A Mouse/Human Chimeric Antibody Directed Against Human Neuroblastoma,", *Int. J. Cancer*, 53:147-152, 1993.
D'Uscio et al., Journal of Immunological Methods, 146:63-70, 1992.
Heuser et al., Gene Therapy, 10:1408-1419, 2003.
Cross et al., Molecular Biology of the Cell, 13:2881-2893, 2002.

* cited by examiner

*Primary Examiner*—David J. Blanchard
(74) *Attorney, Agent, or Firm*—Rothwell, Figg, Ernst & Manbeck P.C.

(57) ABSTRACT

Genetically engineered, CE7-specific redirected immune cells expressing a cell surface protein having an extracellular domain comprising a receptor which is specific for CE7, an intracellular signaling domain, and a transmembrane domain, and methods of use for such cells for cellular immunotherapy of CE7+ neuroblastoma are disclosed. In one embodiment, the immune cell is a T cell and the cell surface protein is a single chain FvFc: ζ receptor where Fv designates the $V_H$ and $V_L$ chains of a single chain monoclonal antibody to CE7 linked by peptide, $F_c$ represents a hinge-$C_H2$-$C_H3$ region of a human $IgG_1$, and ζ represents the intracellular signaling domain of the zeta chain of human CD3. DNA constructs encoding a chimeric T-cell receptor and a method of making a redirected T cell expressing a chimeric T cell receptor by electroporation using naked DNA encoding the receptor are also disclosed.

1 Claim, 13 Drawing Sheets

```
                      (Ori ColE1→)
   1 TGTTAGCGAA GAACATGTGA GCAAAAGGCC AGCAAAAGGC CAGGAACCGT AAAAAGGCCG
     ACAATCGCTT CTTGTACACT CGTTTTCCGG TCGTTTTCCG GTCCTTGGCA TTTTTCCGGC

61 CGTTGCTGGC GTTTTTCCAT AGGCTCCGCC CCCCTGACGA GCATCACAAA AATCGACGCT
     GCAACGACCG CAAAAAGGTA TCCGAGGCGG GGGGACTGCT CGTAGTGTTT TTAGCTGCGA

121 CAAGTCAGAG GTGGCGAAAC CCGACAGGAC TATAAAGATA CCAGGCGTTT CCCCCTGGAA
     GTTCAGTCTC CACCGCTTTG GGCTGTCCTG ATATTTCTAT GGTCCGCAAA GGGGGACCTT

181 GCTCCCTCGT GCGCTCTCCT GTTCCGACCC TGCCGCTTAC CGGATACCTG TCCGCCTTTC
     CGAGGGAGCA CGCGAGAGGA CAAGGCTGGG ACGGCGAATG GCCTATGGAC AGGCGGAAAG

241 TCCCTTCGGG AAGCGTGGCG CTTTCTCATA GCTCACGCTG TAGGTATCTC AGTTCGGTGT
     AGGGAAGCCC TTCGCACCGC GAAAGAGTAT CGAGTGCGAC ATCCATAGAG TCAAGCCACA

301 AGGTCGTTCG CTCCAAGCTG GGCTGTGTGC ACGAACCCCC CGTTCAGCCC GACCGCTGCG
     TCCAGCAAGC GAGGTTCGAC CCGACACACG TGCTTGGGGG GCAAGTCGGG CTGGCGACGC

361 CCTTATCCGG TAACTATCGT CTTGAGTCCA ACCCGGTAAG ACACGACTTA TCGCCACTGG
     GGAATAGGCC ATTGATAGCA GAACTCAGGT TGGGCCATTC TGTGCTGAAT AGCGGTGACC

421 CAGCAGCCAC TGGTAACAGG ATTAGCAGAG CGAGGTATGT AGGCGGTGCT ACAGAGTTCT
     GTCGTCGGTG ACCATTGTCC TAATCGTCTC GCTCCATACA TCCGCCACGA TGTCTCAAGA

481 TGAAGTGGTG GCCTAACTAC GGCTACACTA GAAGAACAGT ATTTGGTATC TGCGCTCTGC
     ACTTCACCAC CGGATTGATG CCGATGTGAT CTTCTTGTCA TAAACCATAG ACGCGAGACG

541 TGAAGCCAGT TACCTTCGGA AAAAGAGTTG GTAGCTCTTG ATCCGGCAAA CAAACCACCG
     ACTTCGGTCA ATGGAAGCCT TTTTCTCAAC CATCGAGAAC TAGGCCGTTT GTTTGGTGGC

601 CTGGTAGCGG TGGTTTTTTT GTTTGCAAGC AGCAGATTAC GCGCAGAAAA AAAGGATCTC
     GACCATCGCC ACCAAAAAAA CAAACGTTCG TCGTCTAATG CGCGTCTTTT TTTCCTAGAG

661 AAGAAGATCC TTTGATCTTT TCTACGGGGT CTGACGCTCA GTGGAACGAA AACTCACGTT
     TTCTTCTAGG AAACTAGAAA AGATGCCCCA GACTGCGAGT CACCTTGCTT TTGAGTGCAA

PacI
                                 ~~~~~~~~~~  (SpAn→)
 721 AAGGGATTTT GGTCATGGCT AGTTAATTAA GCTGCAATAA ACAATCATTA TTTTCATTGG
     TTCCCTAAAA CCAGTACCGA TCAATTAATT CGACGTTATT TGTTAGTAAT AAAAGTAACC

781 ATCTGTGTGT TGGTTTTTTG TGTGGGCTTG GGGGAGGGGG AGGCCAGAAT GACTCCAAGA
     TAGACACACA ACCAAAAAAC ACACCCGAAC CCCCTCCCCC TCCGGTCTTA CTGAGGTTCT

841 GCTACAGGAA GGCAGGTCAG AGACCCCACT GGACAAACAG TGGCTGGACT CTGCACCATA
     CGATGTCCTT CCGTCCAGTC TCTGGGGTGA CCTGTTTGTC ACCGACCTGA GACGTGGTAT

901 ACACACAATC AACAGGGGAG TGAGCTGGAT CGAGCTAGAG TCTCTAGGGC CGCAATAAAA
     TGTGTGTTAG TTGTCCCCTC ACTCGACCTA GCTCGATCTC AGAGATCCCG GCGTTATTTT

961 TATCTTTATT TTCATTACAT CTGTGTGTTG GTTTTTTGTG TGAATCGTAA CTAACATACG
     ATAGAAATAA AAGTAATGTA GACACACAAC CAAAAAACAC ACTTAGCATT GATTGTATGC

1021 CTCTCCATCA AAACAAAACG AAACAAAACA AACTAGCAAA ATAGGCTGTC CCCAGTGCAA
     GAGAGGTAGT TTTGTTTTGC TTTGTTTTGT TTGATCGTTT TATCCGACAG GGGTCACGTT
```

FIG. 1A

```
                                            (hEF1p→)
1081 GTGCAGGTGC CAGAACATTT CTCTATCGAA GGATCTGCGA TCGCTCCGGT GCCCGTCAGT
     CACGTCCACG GTCTTGTAAA GAGATAGCTT CCTAGACGCT AGCGAGGCCA CGGGCAGTCA

1141 GGGCAGAGCG CACATCGCCC ACAGTCCCCG AGAAGTTGGG GGGAGGGGTC GGCAATTGAA
     CCCGTCTCGC GTGTAGCGGG TGTCAGGGGC TCTTCAACCC CCCTCCCCAG CCGTTAACTT

1201 CCGGTGCCTA GAGAAGGTGG CGCGGGGTAA ACTGGGAAAG TGATGTCGTG TACTGGCTCC
     GGCCACGGAT CTCTTCCACC GCGCCCCATT TGACCCTTTC ACTACAGCAC ATGACCGAGG

1261 GCCTTTTTCC CGAGGGTGGG GGAGAACCGT ATATAAGTGC AGTAGTCGCC GTGAACGTTC
     CGGAAAAAGG GCTCCCACCC CCTCTTGGCA TATATTCACG TCATCAGCGG CACTTGCAAG

1321 TTTTTCGCAA CGGGTTTGCC GCCAGAACAC AGCTGAAGCT TCGAGGGGCT CGCATCTCTC
     AAAAAGCGTT GCCCAAACGG CGGTCTTGTG TCGACTTCGA AGCTCCCCGA GCGTAGAGAG

1381 CTTCACGCGC CCGCCGCCCT ACCTGAGGCC GCCATCCACG CCGGTTGAGT CGCGTTCTGC
     GAAGTGCGCG GGCGGCGGGA TGGACTCCGG CGGTAGGTGC GGCCAACTCA GCGCAAGACG

1441 CGCCTCCCGC CTGTGGTGCC TCCTGAACTG CGTCCGCCGT CTAGGTAAGT TTAAAGCTCA
     GCGGAGGGCG GACACCACGG AGGACTTGAC GCAGGCGGCA GATCCATTCA AATTTCGAGT

1501 GGTCGAGACC GGGCCTTTGT CCGGCGCTCC CTTGGAGCCT ACCTAGACTC AGCCGGCTCT
     CCAGCTCTGG CCCGGAAACA GGCCGCGAGG GAACCTCGGA TGGATCTGAG TCGGCCGAGA

1561 CCACGCTTTG CCTGACCCTG CTTGCTCAAC TCTACGTCTT TGTTTCGTTT TCTGTTCTGC
     GGTGCGAAAC GGACTGGGAC GAACGAGTTG AGATGCAGGA ACAAAGCAAA AGACAAGACG

1621 GCCGTTACAG ATCCAAGCTG TGACCGGCGC CTACGTAAGT GATATCTACT AGATTTATCA
     CGGCAATGTC TAGGTTCGAC ACTGGCCGCG GATGCATTCA CTATAGATGA TCTAAATAGT

1681 AAAAGAGTGT TGACTTGTGA GCGCTCACAA TTGATACGG ATTCATCGAG AGGGACACG
     TTTTCTCACA ACTGAACACT CGCGAGTGTT AACTATGCC TAAGTAGCTC TCCCTGTGC

1741 TCGACTACTA ACCTTCTTCT CTTTCCTACA GCTGAGATCA CCGGCGAAGG AGGGGCCCCC
     AGCTGATGAT TGGAAGAAGA GAAAGGATGT CGACTCTAGT GGCCGCTTCC TCCCCGGGGG (CE7R scFvFcZeta→)
         M  L  L  V  T    S  L  L    L  C  E    L  P  H  P
1801 CCTCGAGAGC ACCATGCTTC TCCTGGTGAC AAGCCTTCTG CTCTGTGAGT TACCACACCC
     GGAGCTCTCG TGGTACGAAG AGGACCACTG TTCGGAAGAC GAGACACTCA ATGGTGTGGG . A  F  L    L  I  P    Q  V  Q  L    Q  Q  P    G  A  E    L  V  K  P
1861 AGCATTCCTC CTGATCCCAC AGGTCCAACT GCAGCAGCCT GGGGCTGAAC TGGTGAAGCC
     TCGTAAGGAG GACTAGGGTG TCCAGGTTGA CGTCGTCGGA CCCCGACTTG ACCACTTCGG . G  A  S    V  K  L    S  C  K  A    S  G  Y    T  F  T    G  Y  W  M
1921 TGGGGCTTCA GTGAAGCTGT CCTGCAAGGC TTCTGGCTAC ACCTTCACCG GCTACTGGAT
     ACCCCGAAGT CACTTCGACA GGACGTTCCG AAGACCGATG TGGAAGTGGC CGATGACCTA . H  W  V    K  Q  R    P  G  H  G    L  E  W    I  G  E    I  N  P  S
1981 GCACTGGGTG AAGCAGAGGC CTGGACATGG CCTTGAGTGG ATTGGAGAGA TTAATCCTAG
     CGTGACCCAC TTCGTCTCCG GACCTGTACC GGAACTCACC TAACCTCTCT AATTAGGATC . N  G  R    T  N  Y    N  E  R  F    K  S  K    A  T  L    T  V  D  K
2041 CAACGGTCGT ACTAACTACA ATGAGAGGTT CAAGAGCAAG GCCACACTGA CTGTAGACAA
     GTTGCCAGCA TGATTGATGT TACTCTCCAA GTTCTCGTTC CGGTGTGACT GACATCTGTT
```

FIG. 1B

```
                  · S  S  T    T  A  F    M  Q  L  S    G  L  T    S  E  D    S  A  V  Y
       2101  ATCCTCCACC ACAGCCTTCA TGCAACTCAG CGGCCTGACA TCTGAGGACT CTGCAGTCTA
             TAGGAGGTGG TGTCGGAAGT ACGTTGAGTC GCCGGACTGT AGACTCCTGA GACGTCAGAT

· F  C  A    R  D  Y    Y  G  T  S    Y  N  F    D  Y  W    G  Q  G  T
       2161  TTTCTGTGCA AGAGATTACT ACGGTACTAG CTACAACTTT GACTACTGGG GCCAAGGCAC
             AAAGACACGT TCTCTAATGA TGCCATGATC GATGTTGAAA CTGATGACCC CGGTTCCGTG

· T  L  T    V  S  S    G  G  G  G    S  G  G    G  G  S    G  G  G  G
       2221  CACTCTCACA GTCTCCTCAG GAGGTGGCGG TAGTGGAGGT GGCGGATCCG GTGGCGGAGG
             GTGAGAGTGT CAGAGGAGTC CTCCACCGCC ATCACCTCCA CCGCCTAGGC CACCGCCTCC

· S  D  I    Q  M  T    Q  S  S  S    S  F  S    V  S  L    G  D  R  V
       2281  TAGTGACATC CAGATGACAC AATCTTCATC CTCCTTTTCT GTATCTCTAG AGACAGAGT
             ATCACTGTAG GTCTACTGTG TTAGAAGTAG GAGGAAAAGA CATAGAGATC CTCTGTCTCA

· T  I  T    C  K  A    N  E  D  I    N  N  R    L  A  W    Y  Q  Q  T
       2341  CACCATTACT TGCAAGGCTA ATGAAGACAT AAATAATCGG TTAGCCTGGT ATCAGCAGAC
             GTGGTAATGA ACGTTCCGAT TACTTCTGTA TTTATTAGCC AATCGGACCA TAGTCGTCTG

· P  G  N    S  P  R    L  L  I  S    G  A  T    N  L  V    T  G  V  P
       2401  ACCAGGAAAT TCTCCTAGGC TCTTAATATC TGGTGCAACC AATTTGGTAA CTGGGGTTCC
             TGGTCCTTTA AGAGGATCCG AGAATTATAG ACCACGTTGG TTAAACCATT GACCCCAAGG

· S  R  F    S  G  S    G  S  G  K    D  Y  T    L  T  I    T  S  L  Q
       2461  TTCAAGATTC AGTGGCAGTG GATCTGGAAA GGATTACACT CTCACCATTA CCAGTCTTCA
             AAGTTCTAAG TCACCGTCAC CTAGACCTTT CCTAATGTGA GAGTGGTAAT GGTCAGAAGT

· A  E  D    F  A  T    Y  Y  C  Q    Q  Y  W    S  T  P    F  T  F  G
       2521  GGCTGAAGAT TTTGCTACTT ATTACTGTCA ACAATATTGG AGTACTCCAT TCACGTTCGG
             CCGACTTCTA AAACGATGAA TAATGACAGT TGTTATAACC TCATGAGGTA AGTGCAAGCC

· S  G  T    E  L  E    I  K  V  E    P  K  S    S  D  K    T  H  T  C
       2581  CTCGGGGACA GAGCTCGAGA TCAAAGTAGA ACCCAAATCT TCTGACAAAA CTCACACATG
             GAGCCCCTGT CTCGAGCTCT AGTTTCATCT TGGGTTTAGA AGACTGTTTT GAGTGTGTAC

· P  P  C    P  A  P    E  L  L  G    G  P  S    V  F  L    F  P  P  K
       2641  CCCACCGTGC CCAGCACCTG AACTCCTGGG GGGACCGTCA GTCTTCCTCT TCCCCCCAAA
             GGGTGGCACG GGTCGTGGAC TTGAGGACCC CCCTGGCAGT CAGAAGGAGA AGGGGGGTTT

· P  K  D    T  L  M    I  S  R  T    P  E  V    T  C  V    V  V  D  V
       2701  ACCCAAGGAC ACCCTCATGA TCTCCCGGAC CCCTGAGGTC ACATGCGTGG TGGTGGACGT
             TGGGTTCCTG TGGGAGTACT AGAGGGCCTG GGGACTCCAG TGTACGCACC ACCACCTGCA

· S  H  E    D  P  E    V  K  F  N    W  Y  V    D  G  V    E  V  H  N
       2761  GAGCCACGAA GACCCTGAGG TCAAGTTCAA CTGGTACGTG GACGGCGTGG AGGTGCATAA
             CTCGGTGCTT CTGGGACTCC AGTTCAAGTT GACCATGCAC CTGCCGCACC TCCACGTATT

· A  K  T    K  P  R    E  E  Q  Y    N  S  T    Y  R  V    V  S  V  L
       2821  TGCCAAGACA AAGCCGCGGG AGGAGCAGTA CAACAGCACG TACCGTGTGG TCAGCGTCCT
             ACGGTTCTGT TTCGGCGCCC TCCTCGTCAT GTTGTCGTGC ATGGCACACC AGTCGCAGGA

· T  V  L    H  Q  D    W  L  N  G    K  E  Y    K  C  K    V  S  N  K
       2881  CACCGTCCTG CACCAGGACT GGCTGAATGG CAAGGAGTAC AAGTGCAAGG TCTCCAACAA
             GTGGCAGGAC GTGGTCCTGA CCGACTTACC GTTCCTCATG TTCACGTTCC AGAGGTTGTT
```

FIG. 1C

```
         ·A   L   P    A   P   I    E   K   T    I   S   K   A    K   G   Q    P   R   E   P
2941     AGCCCTCCCA  GCCCCCATCG  AGAAAACCAT  CTCCAAAGCC  AAAGGGCAGC  CCCGAGAACC
         TCGGGAGGGT  CGGGGGTAGC  TCTTTTGGTA  GAGGTTTCGG  TTTCCCGTCG  GGGCTCTTGG

·Q   V   Y    T   L   P    P   S   R   D    E   L   T    K   N   Q    V   S   L   T
3001     ACAGGTGTAC  ACCCTGCCAC  CATCACGAGA  TGAGCTGACC  AAGAACCAGG  TCAGCCTGAC
         TGTCCACATG  TGGGACGGTG  GTAGTGCTCT  ACTCGACTGG  TTCTTGGTCC  AGTCGGACTG

·C   L   V    K   G   F    Y   P   S   D    I   A   V    E   W   E    S   N   G   Q
3061     CTGCCTGGTC  AAAGGCTTCT  ATCCCAGCGA  CATCGCCGTG  GAGTGGGAGA  GCAATGGGCA
         GACGGACCAG  TTTCCGAAGA  TAGGGTCGCT  GTAGCGGCAC  CTCACCCTCT  CGTTACCCGT

·P   E   N    N   Y   K    T   T   P    P   V   L   D    S   D   G    S   F   F   L
3121     GCCGGAGAAC  AACTACAAGA  CCACGCCTCC  CGTGCTGGAC  TCCGACGGCT  CCTTCTTCCT
         CGGCCTCTTG  TTGATGTTCT  GGTGCGGAGG  GCACGACCTG  AGGCTGCCGA  GGAAGAAGGA

·Y   S   K    L   T   V    D   K   S   R    W   Q   Q    G   N   V    F   S   V   S
3181     CTACAGCAAG  CTCACCGTGG  ACAAGAGCAG  GTGGCAGCAG  GGAACGTCT  TCTCATGCTC
         GATGTCGTTC  GAGTGGCACC  TGTTCTCGTC  CACCGTCGTC  CCCTTGCAGA  AGAGTACGAG

·V   M   H    E   A   L    H   N   H   Y    T   Q   K    S   L   S    L   S   P   G
3241     CGTGATGCAT  GAGGCTCTGC  ACAACCACTA  CACGCAGAAG  AGCCTCTCCC  TGTCTCCCGG
         GCACTACGTA  CTCCGAGACG  TGTTGGTGAT  GTGCGTCTTC  TCGGAGAGGG  ACAGAGGGCC

·K   M   A    L   I   V    L   G   G   V    A   G    L   L   F    I   G   L   G
3301     GAAAATGGCC  CTGATTGTGC  TGGGGGGCGT  CGCCGGCCTC  CTGCTTTTCA  TTGGGCTAGG
         CTTTTACCGG  GACTAACACG  ACCCCCCGCA  GCGGCCGGAG  GACGAAAAGT  AACCCGATCC

·I   F   F    R   V   K    F   S   R   S    A   D   A    P   A   Y    Q   Q   G   Q
3361     CATCTTCTTC  AGAGTGAAGT  TCAGCAGGAG  CGCAGACGCC  CCCGCGTACC  AGCAGGGCCA
         GTAGAAGAAG  TCTCACTTCA  AGTCGTCCTC  GCGTCTGCGG  GGGCGCATGG  TCGTCCCGGT

·N   Q   L    Y   N   E    L   N   L   G    R   R   E    E   Y   D    V   L   D   K
3421     GAACCAGCTC  TATAACGAGC  TCAATCTAGG  ACGAAGAGAG  GAGTACGATG  TTTTGGACAA
         CTTGGTCGAG  ATATTGCTCG  AGTTAGATCC  TGCTTCTCTC  CTCATGCTAC  AAAACCTGTT

·R   R   G    R   D   P    E   M   G   G    K   P   R    R   K   N    P   Q   E   G
3481     GAGACGTGGC  CGGGACCCTG  AGATGGGGGG  AAAGCCGAGA  AGGAAGAACC  CTCAGGAAGG
         CTCTGCACCG  GCCCTGGGAC  TCTACCCCCC  TTTCGGCTCT  TCCTTCTTGG  GAGTCCTTCC

·L   Y   N    E   L   Q    K   D   K   M    A   E   A    Y   S   E    I   G   M   K
3541     CCTGTACAAT  GAACTGCAGA  AAGATAAGAT  GGCGGAGGCC  TACAGTGAGA  TTGGGATGAA
         GGACATGTTA  CTTGACGTCT  TTCTATTCTA  CCGCCTCCGG  ATGTCACTCT  AACCCTACTT

·G   E   R    R   R   G    K   G   H   D    G   L   Y    Q   G   L    S   T   A   T
3601     AGGCGAGCGC  CGGAGGGGCA  AGGGGCACGA  TGGCCTTTAC  CAGGGTCTCA  GTACAGCCAC
         TCCGCTCGCG  GCCTCCCCGT  TCCCCGTGCT  ACCGGAAATG  GTCCCAGAGT  CATGTCGGTG

·K   D   T    Y   D   A    L   H   M   Q    A   L   P    P   R
3661     CAAGGACACC  TACGACGCCC  TTCACATGCA  GGCCCTGCCC  CCTCGCTAAG  CGGCCCCTAG
         GTTCCTGTGG  ATGCTGCGGG  AAGTGTACGT  CCGGGACGGG  GGAGCGATTC  GCCGGGGATC
                                 (IRES→)
3721     ATCCTAGATT  GAGTCGACGT  TACTGGCCGA  AGCCGCTTGG  AATAAGGCCG  GTGTGCGTTT
         TAGGATCTAA  CTCAGCTGCA  ATGACCGGCT  TCGGCGAACC  TTATTCCGGC  CACACGCAAA
```

FIG. 1D

```
3781  GTCTATATGT TATTTTCCAC CATATTGCCG TCTTTTGGCA ATGTGAGGGC CCGGAAACCT
      CAGATATACA ATAAAAGGTG GTATAACGGC AGAAAACCGT TACACTCCCG GGCCTTTGGA

3841  GGCCCTGTCT TCTTGACGAG CATTCCTAGG GGTCTTTCCC CTCTCGCCAA AGGAATGCAA
      CCGGGACAGA AGAACTGCTC GTAAGGATCC CCAGAAAGGG GAGAGCGGTT TCCTTACGTT

3901  GGTCTGTTGA ATGTCGTGAA GGAAGCAGTT CCTCTGGAAG CTTCTTGAAG ACAAACAACG
      CCAGACAACT TACAGCACTT CCTTCGTCAA GGAGACCTTC GAAGAACTTC TGTTTGTTGC

3961  TCTGTAGCGA CCCTTTGCAG GCAGCGGAAC CCCCCACCTG GCGACAGGTG CCTCTGCGGC
      AGACATCGCT GGGAAACGTC CGTCGCCTTG GGGGGTGGAC CGCTGTCCAC GGAGACGCCG

4021  CAAAAGCCAC GTGTATAAGA TACACCTGCA AAGGCGGCAC AACCCCAGTG CCACGTTGTG
      GTTTTCGGTG CACATATTCT ATGTGGACGT TTCCGCCGTG TTGGGGTCAC GGTGCAACAC

4081  AGTTGGATAG TTGTGGAAAG AGTCAAATGG CTCTCCTCAA GCGTATTCAA CAAGGGGCTG
      TCAACCTATC AACACCTTTC TCAGTTTACC GAGAGGAGTT CGCATAAGTT GTTCCCCGAC

4141  AAGGATGCCC AGAAGGTACC CCATTGTATG GGATCTGATC TGGGGCCTCG GTGCACATGC
      TTCCTACGGG TCTTCCATGG GGTAACATAC CCTAGACTAG ACCCCGGAGC CACGTGTACG

4201  TTTACATGTG TTTAGTCGAG GTTAAAAAAA CGTCTAGGCC CCCCGAACCA CGGGGACGTG
      AAATGTACAC AAATCAGCTC CAATTTTTTT GCAGATCCGG GGGGCTTGGT GCCCCTGCAC

4261  GTTTTCCTTT GAAAAACACG ATAATACCAT GGGTAAGTGA TATCTACTAG TTGTGACCGG
      CAAAAGGAAA CTTTTTGTGC TATTATGGTA CCCATTCACT ATAGATGATC AACACTGGCC

4321  CGCCTAGTGT TGACAATTAA TCATCGGCAT AGTATATCGG CATAGTATAA TACGACTCAC
      GCGGATCACA ACTGTTAATT AGTAGCCGTA TCATATAGCC GTATCATATT ATGCTGAGTG

4381  TATAGGAGGG CCACCATGTC GACTACTAAC CTTCTTCTCT TTCCTACAGC TGAGATCACC
      ATATCCTCCC GGTGGTACAG CTGATGATTG GAAGAAGAGA AAGGATGTCG ACTCTAGTGG (HyTK→)
                    M  K  K  P  E  L  T  A  T  S  V  A  K  F  L
4441  GGTAGGAGGG CCATCATGAA AAAGCCTGAA CTCACCGCGA CGTCTGTCGC GAAGTTTCTG
      CCATCCTCCC GGTAGTACTT TTTCGGACTT GAGTGGCGCT GCAGACAGCG CTTCAAAGAC

I  E  K  F  D  S  V  S  D  L  M  Q  L  S  E  G  E  E  S  R
4501  ATCGAAAAGT TCGACAGCGT CTCCGACCTG ATGCAGCTCT CGGAGGGCGA AGAATCTCGT
      TAGCTTTTCA AGCTGTCGCA GAGGCTGGAC TACGTCGAGA GCCTCCCGCT TCTTAGAGCA

A  F  S  F  D  V  G  G  R  G  Y  V  L  R  V  N  S  C  A  D
4561  GCTTTCAGCT TCGATGTAGG AGGGCGTGGA TATGTCCTGC GGGTAAATAG CTGCGCCGAT
      CGAAAGTCGA AGCTACATCC TCCCGCACCT ATACAGGACG CCCATTTATC GACGCGGCTA

G  F  Y  K  D  R  Y  V  Y  R  H  F  A  S  A  A  L  P  I  P
4621  GGTTTCTACA AAGATCGTTA TGTTTATCGG CACTTTGCAT CGGCCGCGCT CCCCGATTCCG
      CCAAAGATGT TTCTAGCAAT ACAAATAGCC GTGAAACGTA GCCGGCGCGA GGGCTAAGGC

E  V  L  D  I  G  E  F  S  E  S  L  T  Y  C  I  S  R  R  A
4681  GAAGTGCTTG ACATTGGGGA ATTCAGCGAG AGCCTGACCT ATTGCATCTC CCGCCGTGCA
      CTTCACGAAC TGTAACCCCT TAAGTCGCTC TCGGACTGGA TAACGTAGAG GGCGGCACGT

Q  G  V  T  L  Q  D  L  P  E  T  E  L  P  A  V  L  Q  P  V
4741  CAGGGTGTCA CGTTGCAAGA CCTGCCTGAA ACCGAACTGC CCGCTGTTCT GCAACCCGTC
      GTCCCACAGT GCAACGTTCT GGACGGACTT TGGCTTGACG GGCGACAAGA CGTTGGGCAG
```
FIG. 1E

```
            A  E  L     M  D  A  I     A  A  A     D  L  S     Q  T  S  G     F  G  P
     4801   GCGGAGCTCA  TGGATGCGAT  CGCTGCGGCC  GATCTTAGCC  AGACGAGCGG  GTTCGGCCCA
            CGCCTCGAGT  ACCTACGCTA  GCGACGCCGG  CTAGAATCGG  TCTGCTCGCC  CAAGCCGGGT

F  G  P     Q  G  I  G     Q  Y  T     T  W  R     D  F  I  C     A  I  A
     4861   TTCGGACCGC  AAGGAATCGG  TCAATACACT  ACATGGCGTG  ATTTCATATG  CGCGATTGCT
            AAGCCTGGCG  TTCCTTAGCC  AGTTATGTGA  TGTACCGCAC  TAAAGTATAC  GCGCTAACGA

D  P  H     V  Y  H  W     Q  T  V     M  D  D     T  V  S  A     S  V  A
     4921   GATCCCCATG  TGTATCACTG  GCAAACTGTG  ATGGACGACA  CCGTCAGTGC  GTCCGTCGCG
            CTAGGGGTAC  ACATAGTGAC  CGTTTGACAC  TACCTGCTGT  GGCAGTCACG  CAGGCAGCGC

Q  A  L     D  E  L  M     L  W  A     E  D  C     P  E  V  R     H  L  V
     4981   CAGGCTCTCG  ATGAGCTGAT  GCTTTGGGCC  GAGGACTGCC  CCGAAGTCCG  GCACCTCGTG
            GTCCGAGAGC  TACTCGACTA  CGAAACCCGG  CTCCTGACGG  GGCTTCAGGC  CGTGGAGCAC

H  A  D     F  G  S  N     N  V  L     T  D  N     G  R  I  T     A  V  I
     5041   CACGCGGATT  TCGGCTCCAA  CAATGTCCTG  ACGGACAATG  GCCGCATAAC  AGCGGTCATT
            GTGCGCCTAA  AGCCGAGGTT  GTTACAGGAC  TGCCTGTTAC  CGGCGTATTG  TCGCCAGTAA

D  W  S     E  A  M  F     G  D  S     Q  Y  E     V  A  N  I     F  F  W
     5101   GACTGGAGCG  AGGCGATGTT  CGGGGATTCC  CAATACGAGG  TCGCCAACAT  CTTCTTCTGG
            CTGACCTCGC  TCCGCTACAA  GCCCCTAAGG  GTTATGCTCC  AGCGGTTGTA  GAAGAAGACC

R  P  W     L  A  C  M     E  Q  Q     T  R  Y     F  E  R  R     H  P  E
     5161   AGGCCGTGGT  TGGCTTGTAT  GGAGCAGCAG  ACGCGCTACT  TCGAGCGGAG  GCATCCGGAG
            TCCGGCACCA  ACCGAACATA  CCTCGTCGTC  TGCGCGATGA  AGCTCGCCTC  CGTAGGCCTC

L  A  G     S  P  R  L     R  A  Y     M  L  R     I  G  L  D     Q  L  Y
     5221   CTTGCAGGAT  CGCCGCGGCT  CCGGGCGTAT  ATGCTCCGCA  TTGGTCTTGA  CCAACTCTAT
            GAACGTCCTA  GCGGCGCCGA  GGCCCGCATA  TACGAGGCGT  AACCAGAACT  GGTTGAGATA

Q  S  L     V  D  G  N     F  D  D     A  A  W     A  Q  G  R     C  D  A
     5281   CAGAGCTTGG  TTGACGGCAA  TTTCGATGAT  GCAGCTTGGG  CGCAGGGTCG  ATGCGACGCA
            GTCTCGAACC  AACTGCCGTT  AAAGCTACTA  CGTCGAACCC  GCGTCCCAGC  TACGCTGCGT

I  V  R     S  G  A  G     T  V  G     R  T  Q     I  A  R  R     S  A  A
     5341   ATCGTCCGAT  CCGGAGCCGG  GACTGTCGGG  CGTACACAAA  TCGCCCGCAG  AAGCGCGGCC
            TAGCAGGCTA  GGCCTCGGCC  CTGACAGCCC  GCATGTGTTT  AGCGGGCGTC  TTCGCGCCGG

V  W  T     D  G  C  V     E  V  A     S  A  F     D  Q  A  A     R  S  R
     5401   GTCTGGACCG  ATGGCTGTGT  AGAAGTCGCG  TCTGCGTTCG  ACCAGGCTGC  GCGTTCTCGC
            CAGACCTGGC  TACCGACACA  TCTTCAGCGC  AGACGCAAGC  TGGTCCGACG  CGCAAGAGCG

G  H  S     N  R  R  T     A  L  R     P  R  R     Q  Q  E  A     T  E  V
     5461   GGCCATAGCA  ACCGACGTAC  GGCGTTGCGC  CCTCGCCGGC  AGCAAGAAGC  CACGGAAGTC
            CCGGTATCGT  TGGCTGCATG  CCGCAACGCG  GGAGCGGCCG  TCGTTCTTCG  GTGCCTTCAG

R  P  E     Q  K  M  P     T  L  L     R  V  Y     I  D  G  P     H  G  M
     5521   CGCCCGGAGC  AGAAAATGCC  CACGCTACTG  CGGGTTTATA  TAGACGGTCC  CCACGGGATG
            GCGGGCCTCG  TCTTTTACGG  GTGCGATGAC  GCCCAAATAT  ATCTGCCAGG  GGTGCCCTAC

G  K  T     T  T  T  Q     L  L  V     A  L  G     S  R  D  D     I  V  Y
     5581   GGGAAAACCA  CCACCACGCA  ACTGCTGGTG  GCCCTGGGTT  CGCGCGACGA  TATCGTCTAC
            CCCTTTTGGT  GGTGGTGCGT  TGACGACCAC  CGGGACCCAA  GCGCGCTGCT  ATAGCAGATG
```

FIG. 1F

```
              V   P   E       P   M   T   Y       W   R   V       L   G   A       S   E   T   I       A   N   I
       5641  GTACCCGAGC CGATGACTTA CTGGCGGGTG CTGGGGGCTT CCGAGACAAT CGCGAACATC
             CATGGGCTCG GCTACTGAAT GACCGCCCAC GACCCCCGAA GGCTCTGTTA GCGCTTGTAG

Y   T   T       Q   H   R   L       D   Q   G       E   I   S       A   G   D       A   V   V
       5701  TACACCACAC AACACCGCCT CGACCAGGGT GAGATATCGG CCGGGGACGC GGCGGTGGTA
             ATGTGGTGTG TTGTGGCGGA GCTGGTCCCA CTCTATAGCC GGCCCCTGCG CCGCCACCAT

M   T   S       A   Q   I   T       M   G   M       P   Y   A       V   T   D       A   V   L   A
       5761  ATGACAAGCG CCCAGATAAC AATGGGCATG CCTTATGCCG TGACCGACGC CGTTCTGGCT
             TACTGTTCGC GGGTCTATTG TTACCCGTAC GGAATACGGC ACTGGCTGCG GCAAGACCGA

P   H   I       G   G   E   A       G   S   S       H   A   P       P   P   A   L       T   L   I
       5821  CCTCATATCG GGGGGGAGGC TGGGAGCTCA CATGCCCCGC CCCCGGCCCT CACCCTCATC
             GGAGTATAGC CCCCCCTCCG ACCCTCGAGT GTACGGGGCG GGGGCCGGGA GTGGGAGTAG

F   D   R       H   P   I   A       A   L   L       C   Y   P       A   A   R   Y       L   M   G
       5881  TTCGACCGCC ATCCCATCGC CGCCCTCCTG TGCTACCCGG CCGCGCGGTA CCTTATGGGC
             AAGCTGGCGG TAGGGTAGCG GCGGGAGGAC ACGATGGGCC GGCGCGCCAT GGAATACCCG

S   M   T       P   Q   A   V       L   A   F       V   A   L       I   P   P   T       L   P   G
       5941  AGCATGACCC CCCAGGCCGT GCTGGCGTTC GTGGCCCTCA TCCCGCCGAC CTTGCCCGGC
             TCGTACTGGG GGGTCCGGCA CGACCGCAAG CACCGGGAGT AGGGCGGCTG GAACGGGCCG

T   N   I       V   L   G   A       L   P   E       D   R   H       I   D   R   L       A   K   R
       6001  ACCAACATCG TGCTTGGGGC CCTTCCGGAG GACAGACACA TCGACCGCCT GGCCAAACGC
             TGGTTGTAGC ACGAACCCCG GGAAGGCCTC CTGTCTGTGT AGCTGGCGGA CCGGTTTGCG

Q   R   P       G   E   R   L       D   L   A       M   L   A       I   R   R       V   Y   G
       6061  CAGCGCCCCG GCGAGCGGCT GGACCTGGCT ATGCTGGCTG CGATTCGCCG CGTTTACGGG
             GTCGCGGGGC CGCTCGCCGA CCTGGACCGA TACGACCGAC GCTAAGCGGC GCAAATGCCC

L   L   A       N   T   V   R       Y   L   Q       C   G   G       S   W   R   E       D   W   G
       6121  CTACTTGCCA ATACGGTGCG GTATCTGCAG TGCGGCGGGT CGTGGCGGGA GGACTGGGGA
             GATGAACGGT TATGCCACGC CATAGACGTC ACGCCGCCCA GCACCGCCCT CCTGACCCCT

Q   L   S       G   T   A   V       P   P   Q       G   A   E       P   Q   S   N       A   G   P
       6181  CAGCTTTCGG GGACGGCCGT GCCGCCCCAG GGTGCCGAGC CCCAGAGCAA CGCGGGCCCA
             GTCGAAAGCC CCTGCCGGCA CGGCGGGGTC CCACGGCTCG GGGTCTCGTT GCGCCCGGGT

R   P   H       I   G   D   T       L   F   T       L   F   R       A   P   E   L       L   A   P
       6241  CGACCCCATA TCGGGGACAC GTTATTTACC CTGTTTCGGG CCCCCGAGTT GCTGGCCCCC
             GCTGGGGTAT AGCCCCTGTG CAATAAATGG GACAAAGCCC GGGGGCTCAA CGACCGGGGG

N   G   D       L   Y   N   V       F   A   W       A   L   D       V   L   A   K       R   L   R
       6301  AACGGCGACC TGTATAACGT GTTTGCCTGG GCCTTGGACG TCTTGGCCAA ACGCCTCCGT
             TTGCCGCTGG ACATATTGCA CAAACGGACC CGGAACCTGC AGAACCGGTT TGCGGAGGCA

S   M   H       V   F   I   L       D   Y   D       Q   S   P       A   G   C   R       D   A   L
       6361  TCCATGCACG TCTTTATCCT GGATTACGAC CAATCGCCCG CCGGCTGCCG GGACGCCCTG
             AGGTACGTGC AGAAATAGGA CCTAATGCTG GTTAGCGGGC GGCCGACGGC CCTGCGGGAC

L   Q   L       T   S   G   M       V   Q   T       H   V   T       T   P   G   S       I   P   T
       6421  CTGCAACTTA CCTCCGGGAT GGTCCAGACC CACGTCACCA CCCCCGGCTC CATACCGACG
             GACGTTGAAT GGAGGCCCTA CCAGGTCTGG GTGCAGTGGT GGGGGCCGAG GTATGGCTGC
```

FIG. 1G

```
            I   C   D   L   A   R   T   F   A   R   E   M   G   E   A   N   *   (bGh pAN→)
6481 ATATGCGACC TGGCGCGCAC GTTTGCCCGG GAGATGGGGG AGGCTAACTG AGTCGAGAAT
     TATACGCTGG ACCGCGCGTG CAAACGGGCC CTCTACCCCC TCCGATTGAC TCAGCTCTTA

6541 TCGCTAGAGG GCCCTATTCT ATAGTGTCAC CTAAATGCTA GAGCTCGCTG ATCAGCCTCG
     AGCGATCTCC CGGGATAAGA TATCACAGTG GATTTACGAT CTCGAGCGAC TAGTCGGAGC

6601 ACTGTGCCTT CTAGTTGCCA GCCATCTGTT GTTTGCCCCT CCCCCGTGCC TTCCTTGACC
     TGACACGGAA GATCAACGGT CGGTAGACAA CAAACGGGGA GGGGGCACGG AAGGAACTGG

6661 CTGGAAGGTG CCACTCCCAC TGTCCTTTCC TAATAAAATG AGGAAATTGC ATCGCATTGT
     GACCTTCCAC GGTGAGGGTG ACAGGAAAGG ATTATTTTAC TCCTTTAACG TAGCGTAACA

6721 CTGAGTAGGT GTCATTCTAT TCTGGGGGGT GGGGTGGGGC AGGACAGCAA GGGGGAGGAT
     GACTCATCCA CAGTAAGATA AGACCCCCCA CCCCACCCCG TCCTGTCGTT CCCCCTCCTA

6781 TGGGAAGACA ATAGCAGGCA TGCGCAGGGC CCAATTGCTC GAGCGATCTA TCGAAA
     ACCCTTCTGT TATCGTCCGT ACGCGTCCCG GGTTAACGAG CTCGCTAGAT AGCTTT
```

FIG. 1H

CE7-SPECIFIC CHIMERIC T CELL RECEPTOR

CROSS-REFERENCE TO RELATED APPLICATIONS

This application is a division of U.S. patent application Ser. No. 10/120,198 filed 11 Apr. 2002, now U.S. Pat. No. 7,070,995, Ser. No. 10/120,198 is related to claims priority under 35 U.S.C. §119(e) to U.S. provisional patent application Ser. No. 60/282,859 filed 11 Apr. 2001. Each application is incorporated herein by reference.

BACKGROUND OF THE INVENTION

This invention relates to the field of genetically engineered, redirected immune cells and to the field of cellular immunotherapy of CE7 malignancies.

The publications and other materials used herein to illuminate the background of the invention or provide additional details respecting the practice are incorporated by reference.

Neuroblastoma, a neoplasm arising from sympathetic ganglion cells, is the most common extracranial solid tumor of childhood and is third in incidence among pediatric malignancies after the leukemia-lymphoma syndromes and central nervous system tumors [1-2]. Approximately 550 new cases occur annually in the United States; seventy-nine percent of children are diagnosed prior to their fifth birthday. Stage of disease at diagnosis, patient's age at diagnosis, and characteristics of tumor cells such as histologic appearance and NMYC gene amplification are important prognostic factors which can be utilized to categorize patients into low, intermediate and high risk for poor outcome [3, 4]. While survival for low and intermediate risk neuroblastoma is excellent, the prognosis for high-risk neuroblastoma remains dismal. Despite improved tumor response rates following intensive multi-modality therapy the median response duration of high risk tumors is less than 1 year and less than 40% of patients with high risk neuroblastoma survive more than 2 years [3-6]. To date there are no treatment modalities with proven efficacy for salvaging children with recurrent/refractory disseminated neuroblastoma.

Current treatment strategies for neuroblastoma are tailored to risk-stratified algorithms based on the International Neuroblastoma Staging System (INSS) [6-9]. The primary risk factors accounted for are age at diagnosis, stage of disease, tumor histology, NMYC copy number, and DNA index. High-risk disease includes those children greater than twelve months of age with tumor dissemination (Stage IV) as well as Stage 3 and 4 disease with unfavorable histology or NMYC amplification, regardless of age [10-17]. High-risk disease accounts for more than half of newly diagnosed cases of neuroblastoma and approximately three-quarters of cases diagnosed in children greater than 12 months of age. A multi-modality maximally intensive approach to treatment of high-risk neuroblastoma has evolved that includes aggressive induction chemotherapy, surgery, radiation therapy, autologous stem cell transplantation, and post-transplant biologic therapy with cis-retinoic acid. Two successive Children's Cancer Group trials (CCG-321, CCG-3891) have demonstrated improved survival for those patients receiving myelo-ablative therapy compared to those patients receiving conventional chemotherapy [18]. Aggressive local therapy including complete surgical resection of the primary tumor and local radiation appears to decrease the incidence of primary site recurrence. Unfortunately, more than 50% of all patients and 75% of patients failing to achieve a complete remission with $1^{st}$ line conventional therapy continue to develop recurrent disease. Relapses typically occur in a disseminated fashion within the first 24-months after completing front-line therapy. Responses to salvage chemotherapy are limited and generally are not durable with only 8% of patients surviving greater that 3 years from time of recurrence [19-23].

Disease relapse for many children with neuroblastoma frequently occurs following the induction of a clinical complete response with standard treatment modalities, demonstrating that the persistence of minimal residual disease is a major obstacle for curative therapy. However, patients heavily treated with chemotherapy, radiation, surgery, and autologous transplantation have a limited capacity to tolerate additional cytotoxic therapeutic modalities to target minimal residual disease. The potential of targeting a limited tumor burden with immune-based approaches is attractive both, because of the opportunity to invoke immunologic effector mechanisms to which chemotherapy/radiation-resistant tumor cells are susceptible, as well as the limited toxicity theoretically possible with tumor-specific immunologic effector mechanisms.

Passive immunotherapy for neuroblastoma utilizing murine monoclonal and murine/human chimeric monoclonal antibodies have focused primarily on targeting the $G_{D2}$ disialoganglioside present at high density on human NB [24-26]. Cheung et al. have investigated in clinical trials the $G_{D2}$-specific monoclonal antibody 3F8 and have reported on the safety and, more recently, the anti-tumor activity of antibody therapy in the setting of minimal residual disease [27]. The long-term outcome of patients treated with 3F8 awaits delineation, however, limitations in its use have been observed early after treatment due to the development of neutralizing HAMA responses in approximately a third of patients [27]. Additionally, failure of antibody therapy to target MRD in the CNS due to poor penetration of immunoglobulin across the blood-brain-barrier was manifested by an unusually high incidence of isolated CNS relapses in antibody treated patients.

The cloning and production of recombinant cytokines have facilitated their introduction into clinical trials designed to activate and expand immunologic effector cells in vivo. Various cytokines either alone or in combination have been evaluated in preclinical neuroblastoma animal models [28-30]. Interleukin-2 administration following transplantation has been most extensively studied as a strategy to activate NK cells and induce LAK cells. IL-2 therapy for patients with recurrent metastatic neuroblastoma failed to provide anti-tumor activity in 15 children treated [31,32]. These studies to date have revealed a significant incidence of severe toxicities associated with high-dose IL-2 administration without a clear impact on decreasing disease relapse. The prolonged use of low-dose IL-2, although not having demonstrable anti-neuroblastoma activity, can be administered to heavily pre-treated children without severe toxicity [33]. Pession et al. have reported on the administration of 212 courses of low dose IL-2 to 17 children with neuroblastoma following stem cell transplantation [33]. These maintenance courses were delivered bimonthly over five days/course at IL-2 doses of $2 \times 10^6$ U/m²/day escalating to $4 \times 10^6$ U/m²/day. No life-threatening toxicities were encountered. Fever controlled by acetaminophen and transient rash were the most common side effects of therapy. Consequently, current Phase I studies are evaluating the combination of cytokines that activate effector cells operative in antibody dependent cellular cytotoxicity (IL-2 and GM-CSF) in combination with anti-$G_{D2}$ antibody therapy

[34,35]. Frost et al. have investigated the use of monoclonal anti-GD2 antibody, 14.G2a plus IL-2 in 31 children with refractory neuroblastoma. Dose limiting toxicities included generalized pain and fever without documented infection. Tumor progression was noted in 63% of patients. Of note, 30% of patients with evaluable bone marrow disease had a significant decrease in quantity of tumor cells detected by immunohistochemical analysis [35]. The engineering of antibody-cytokine fusion molecules appears to potentiate the anti-tumor activity of either molecule administered separately in animal models, these fusion proteins are currently under investigation in clinical trials [36,37].

Induction or augmentation of a cellular immune response against neuroblastoma is an attractive strategy for eliminating resistant tumor cells. The availability of recombinant interleukin-2 (IL-2) and the demonstration that lymphocytes cultured in high concentrations of lymphokines acquire the ability to lyse, in a non-MHC-restricted fashion, a variety of tumor types, led to trials attempting to target neuroblastoma with the adoptive transfer of autologous ex-vivo expanded LAK cells [38]. Up to $10^{11}$ LAK cells have been administered in a single intravenous infusion to cancer patients without dose-limiting side effects, demonstrating the safety of adoptive therapy with large numbers of in vitro activated autologous lymphocytes. The toxicity that has been observed in these trials was attributed solely to the systemic effects of high-dose IL-2 that is required to support LAK cells in vivo [39]. LAK cell therapy in children with neuroblastoma has met with significant toxicities without obvious clinical benefit [31].

Animal models as well as a small but growing number of human tumor systems have demonstrated that anti-tumor cellular immune responses can be invoked or amplified by vaccination with tumor cells genetically modified to have enhanced immunogenicity. Transgenes that are being evaluated for neuroblastoma tumor cell vaccines include allogeneic HLA class II molecules, the co-stimulatory ligand B7-1, and pro-inflammatory cytokines [40-46]. Recently Bowman et al. published their results of a pilot study in which ten children with relapsed advanced stage neuroblastoma were treated with autologous tumor cells genetically modified to secrete IL-2 [47]. Of note, five patients had objective systemic anti-tumor responses correlating with the development of in vitro detected anti-tumor cellular cytotoxicity. These studies provide a glimpse at the potential of cellular immunotherapy for neuroblastoma but underscore the variability of inducing clinically relevant anti-tumor responses with vaccines and the technical difficulties in generating autologous genetically manipulated tumor cell lines for this application.

Antigen-specific T cells are immunologic effector cells that confer protection from lethal tumor challenge in animal models [48]. Adoptive transfer of tumor-specific T cell clones into tumor bearing hosts can eradicate established disseminated tumors. Enomoto et al. have demonstrated in a murine model system employing a poorly immunogenic syngeneic neuroblastoma, the capacity of adoptively transferred tumor-reactive cytotoxic T lymphocytes (CTL) to eradicate disseminated neuroblastoma [49]. This provocative model system, in light of the responses seen clinically to IL-2 producing tumor vaccine administration, suggest that adoptive therapy with neuroblastoma-specific T cells may have significant clinical utility provided these T cells can be reliably isolated from this patient population.

An ideal cell-surface epitope for targeting with antigen-specific T cells would be expressed solely on tumor cells in a homogeneous fashion and on all tumors within a population of patients with the same diagnosis. Modulation and/or shedding of the target molecule from the tumor cell membrane may also impact on the utility of a particular target epitope for re-directed T cell recognition. To date few "ideal" tumor-specific epitopes have been defined and secondary epitopes have been targeted based on either lack of expression on critical normal tissues or relative over-expression on tumors. Anti-$G_{D2}$ antibodies have been most extensively utilized in antigen-specific immunotherapy for neuroblastoma. $G_{D2}$, however, is expressed on peripheral nerves as well as brain grey matter. T cells, unlike antibody, can extensively access the CNS blood-brain barrier making $G_{D2}$ re-directed adoptive T cell therapy subject to potentially severe neurologic toxicities [50].

Several groups have generated murine monoclonal antibodies reactive with human neuroblastoma by immunization of mice with human NB tumor cell lines. Blaser et al. have published on the generation of the CE7 monoclonal antibody (γI/κ) raised by immunizing mice with the IMR-32 human neuroblastoma cell line. CE7 uniformly binds to human neuroblastoma cell lines and primary tumors [51-53]. This high affinity IgGI monoclonal antibody ($K_a=10^{-11}$) precipitates a 190-kDA plasma membrane-associated glycoprotein [54]. Tumor cells express in excess of 40,000 binding epitopes for CE7 and the target molecule does not shed from the cell surface. Biodistribution studies in nude mice revealed that up to 32% of injected dose/g tissue of iodinated antibody accumulates in tumor explants with low blood and organ uptake [55,56]. Importantly, this antibody in immunohistochemistry screening of normal tissues failed to bind to all non-neuroectodermal tissues as well as brain [51]. Very weak binding was observed on adrenal medulla and sympathetic ganglia [50]. Carrel et al. have generated a mouse/human chimeric antibody and are pursuing preclinical studies for development of CE7-targeted radioimmunotherapy for neuroblastoma [56]. As with many monoclonal antibodies raised against tumor cell lines, the molecular identity of the target epitope of CE7 awaits delineation.

The safety of adoptively transferring antigen-specific CTL clones in humans was originally examined in bone marrow transplant patients who received donor-derived CMV-specific T cells [57,80]. Studies from the laboratories of Drs. Greenberg and Riddell at the Fred Hutchinson Cancer Research Center (FHCRC) have demonstrated that the reconstitution of endogenous CMV-specific T cell responses following allogeneic bone marrow transplantation (BMT) correlates with protection from the development of severe CMV disease [58]. In an effort to reconstitute deficient CMV immunity following BMT, $CD8^+$ CMV-specific CTL clones were generated from CMV seropositive HLA-matched sibling donors, expanded, and infused into sibling BMT recipients at risk for developing CMV disease. Fourteen patients were treated with four weekly escalating doses of these CMV-specific CTL clones to a maximum cell dose of $10^9$ cells/m$^2$ without any attendant toxicity [59]. Peripheral blood samples obtained from recipients of adoptively transferred T cell clones were evaluated for in vivo persistence of transferred cells. The recoverable CMV-specific CTL activity increased after each successive infusion of CTL clones, and persisted at least 12 weeks after the last infusion. However, long term persistence of $CD8^+$ clones without a concurrent $CD4^+$ helper response was not observed. No patients developed CMV viremia or disease. These results demonstrate that ex-vivo expanded CMV-specific CTL clones can be safely transferred to BMT recipients and can persist in vivo as functional effector cells that may provide protection from the development of CMV disease.

A complication of bone marrow transplantation, particularly when marrow is depleted of T cells, is the development of EBV-associated lymphoproliferative disease [60]. This rapidly progressive proliferation of EBV-transformed B-cells mimics immunoblastic lymphoma and is a consequence of deficient EBV-specific T cell immunity in individuals harboring latent virus or immunologically naïve individuals receiving a virus inoculum with their marrow graft. Clinical trials conducted at St. Jude's Hospital by Rooney et al. have demonstrated that adoptively transferred ex-vivo expanded donor-derived EBV-specific T cell lines can protect patients at high risk for development of this complication as well as mediate the eradication of clinically evident EBV-transformed B cells [61]. No significant toxicities were observed in the forty-one children treated with cell doses in the range of $4 \times 10^7$ to $1.2 \times 10^8$ cells/m$^2$.

Genetic modification of T cells used in clinical trials has been utilized to mark cells for in vivo tracking and to endow T cells with novel functional properties. Retroviral vectors have been used most extensively for this purpose due to their relatively high transduction efficiency and low in vitro toxicity to T cells [62]. These vectors, however, are time consuming and expensive to prepare as clinical grade material and must be meticulously screened for the absence of replication competent viral mutants [63]. Rooney et al. transduced EBV-reactive T cell lines with the NeoR gene to facilitate assessment of cell persistence in vivo by PCR specific for this marker gene [64]. Riddell et al. have conducted a Phase I trial to augment HIV-specific immunity in HIV seropositive individuals by adoptive transfer using HIV-specific CD8$^+$ CTL clones [65]. These clones were transduced with the retroviral vector tgLS$^+$HyTK which directs the synthesis of a bifunctional fusion protein incorporating hygromycin phosphotransferase and herpes virus thymidine kinase (HSV-TK) permitting in vitro selection with hygromycin and potential in vivo ablation of transferred cells with gancyclovir. Six HIV infected patients were treated with a series of four escalating cell dose infusions without toxicities, with a maximum cell dose of $5 \times 10^9$ cells/m$^2$ [65].

As an alternate to viral gene therapy vectors, Nabel et al. used plasmid DNA encoding an expression cassette for an anti-HIV gene in a Phase I clinical trial. Plasmid DNA was introduced into T cells by particle bombardment with a gene gun [66]. Genetically modified T cells were expanded and infused back into HIV-infected study subjects. Although this study demonstrated the feasibility of using a non-viral genetic modification strategy for primary human T cells, one limitation of this approach is the episomal propagation of the plasmid vector in T cells. Unlike chromosomally integrated transferred DNA, episomal propagation of plasmid DNA carries the risk of loss of transferred genetic material with cell replication and of repetitive random chromosomal integration events.

Chimeric antigen receptors engineered to consist of an extracellular single chain antibody (scFvFc) fused to the intracellular signaling domain of the T cell antigen receptor complex zeta chain (ζ) have the ability, when expressed in T cells, to redirect antigen recognition based on the monoclonal antibody's specificity [67]. The design of scFvFc: ζ receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen positive tumors. Several constructs for targeting human tumors have been described in the literature including receptors with specificities for Her2/Neu, CEA, ERRB-2, CD44v6, and epitopes selectively expressed on renal cell carcinoma [68-72]. These epitopes all share the common characteristic of being cell-surface moieties accessible to scFv binding by the chimeric T cell receptor. In vitro studies have demonstrated that both CD4$^+$ and CD8$^+$ T cell effector functions can be triggered via these receptors. Moreover, animal models have demonstrated the capacity of adoptively transferred scFvFc: ζ expressing T cells to eradicate established tumors [73]. The function of primary human T cells expressing tumor-specific scFvFc: ζ receptors have been evaluated in vitro; these cells specifically lyse tumor targets and secrete an array of pro-inflammatory cytokines including IL-2, TNF, IFN-g, and GM-CSF [74]. Phase I pilot adoptive therapy studies are underway utilizing autologous scFvFc: ζ-expressing T cells specific for HIV gp120 in HIV infected individuals and autologous scFvFc: ζ-expressing T cells with specificity for TAG-72 expressed on a variety of adenocarcinomas including breast and colorectal adenocarcinoma.

Investigators at City of Hope have engineered a CD20-specific scFvFc: ζ receptor construct for the purpose of targeting CD20+ B-cell malignancy [75]. Preclinical laboratory studies have demonstrated the feasibility of isolating and expanding from healthy individuals and lymphoma patients CD8+ CTL clones that contain a single copy of unrearranged chromosomally integrated vector DNA and express the CD20-specific scFvFc: ζ receptor [76]. To accomplish this, purified linear plasmid DNA containing the chimeric receptor sequence under the transcriptional control of the CMV immediate/early promoter and the NeoR gene under the transcriptional control of the SV40 early promoter was introduced into activated human peripheral blood mononuclear cells by exposure of cells and DNA to a brief electrical current, a procedure called electroporation [77]. Utilizing selection, cloning, and expansion methods currently employed in FDA-approved clinical trials, gene modified CD8+ CTL clones with CD20-specific cytolytic activity have been generated from each of six healthy volunteers in 15 separate electroporation procedures [76]. These clones when co-cultured with a panel of human CD20+ lymphoma cell lines proliferate, specifically lyse target cells, and are stimulated to produce cytokines.

It is desired to develop additional redirected immune cells and, in a preferred embodiment redirected T cells for treating neuroblastoma and other malignancies expressing the CE7 recognized target epitope.

SUMMARY OF THE INVENTION

In one aspect, the present invention provides genetically engineered immune cells (referred to herein as CE7-specific redirected immune cells) which express and bear on the cell surface membrane a CE7-specific chimeric immune receptor (referred to also as CE7R) comprising an intracellular signaling domain, a transmembrane domain (TM) and a CE7-specific extracellular domain (domain derived from the variable heavy and light chain regions of the CE7 monoclonal antibody). The present invention also provides the CE7-specific chimeric immune receptors, DNA constructs encoding the receptors, and plasmid expression vectors containing the constructs in proper orientation for expression.

In a second aspect, the present invention provides a method of treating a CE7+ malignancy in a mammal (i.e., those malignancies which express the CE7 recognized target epitope) which comprises administering CE7-specific redirected immune cells to the mammal in a therapeutically effective amount. In one embodiment, CD8+ CE7-specific redirected T cells are administered, preferably with CD4+ CE7-specific redirected T cells. In a second embodiment, CD+4CE7-specific redirected T cells are administered to a mammal (preferably in combination with CD8+ cytotoxic lymphocytes which express the CE7-specific chimeric receptor).

In a third aspect, the present invention provides a method of making and expanding the CE7-specific redirected T cells which comprises transfecting T cells with an expression vector containing a DNA construct encoding the CE7-specific chimeric receptor, then stimulating the cells with CE7+cells, recombinant CE7, or an antibody to the receptor to cause the cells to proliferate. In one embodiment, the redirected T cells are prepared by electroporation. In a second embodiment, the redirected T cells are prepared by using viral vectors.

In another aspect, the invention provides genetically engineered stem cells which express on their surface membrane a CE7-specific chimeric immune receptor having an intracellular signaling domain, a transmembrane domain and a CE7-specific extracellular domain.

In another aspect, the invention provides genetically engineered natural killer(NK) cells which express on their surface membrane a CE7-specific chimeric immune receptor having an intracellular signaling domain, a transmembrane domain and a CE7-specific extracellular domain.

In another aspect, the invention provides genetically engineered neutrophils which express on their surface membrane a CE7-specific chimeric immune receptor having an intracellular signaling domain, a transmembrane domain and a CE7-specific extracellular domain.

In yet another aspect, the invention provides genetically engineered macrophage which express on their surface membrane a CE7-specific chimeric immune receptor having an intracellular signaling domain, a transmembrane domain and a CE7-specific extracellular domain.

BRIEF DESCRIPTION OF THE FIGURES

FIGS. 1A, 1B, 1C, 1D, 1E, 1F, 1G and 1H show the double-stranded DNA sequence of the plasmid containing a CE7R chimeric immunoreceptor of the present invention and show the source of the DNA found in the plasmid. The amino acid sequences of the CE7R/HyTK are also shown. The sense strand of the double-stranded DNA sequence is set forth in SEQ ID NO:5. The sense strand of the double stranded sequence coding for the CE7R chimeric receptor is set forth in SEQ ID NO:1, and the corresponding amino acid sequence is set forth in SEQ ID NO:2. The sense strand of the double stranded sequence coding for HyTK is set forth in SEQ ID NO:3, and the corresponding amino acid sequence is set forth in SEQ ID NO:4.

DETAILED DESCRIPTION OF THE INVENTION

Figure 2A:
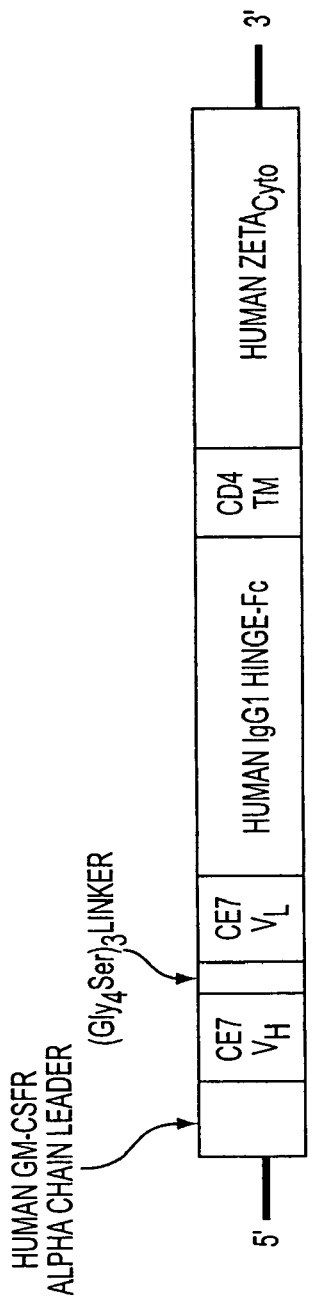
FIG. 2A is a schematic representation of a CE7R/scFvFc: ζ chimeric receptor.

The present invention is directed to genetically engineered, redirected immune cells and to their use for cellular immunotherapy of malignancies which express the CE7 recognized target epitope, including, but not limited to, neuroblastoma.

In one aspect, the present invention provides genetically engineered T cells which express and bear on the cell surface membrane a CE7-specific chimeric T-cell receptor having an intracellular signaling domain, a transmembrane domain and a CE7-specific extracellular domain. The extracellular domain comprises a CE7-specific receptor. Individual T cells of the invention may be CD4+/CD8−, CD4−/CD8+, CD4−/CD8− or CD4+/CD8+. The T cells may be a mixed population of CD4+/CD8− and CD4−/CD8+ cells or a population of a single clone. CD4+ T cells of the invention produce IL-2 when co-cultured in vitro with CE7+ neuroblastoma cells. CD8+ T cells of the invention lyse CE7+ human neuroblastoma target cells when co-cultured in vitro with the target cells. The invention further provides the CE7-specific chimeric T-cell receptors, DNA constructs encoding the receptors, and plasmid expression vectors containing the constructs in proper orientation for expression.

In a preferred embodiment, the CE7-specific redirected T cells express CE7-specific chimeric receptor scFvFc: ζ, where scFv designates the $V_H$ and $V_L$ chains of a single chain monoclonal antibody to CE7, Fc represents at least part of a constant region of an IgG$_1$, and ζ represents the intracellular signaling domain of the zeta chain of the human CD3 complex. The extracellular domain scFvFc and the intracellular domain ζ are linked by a transmembrane (TM) domain such as the transmembrane domain of CD4. In a specific preferred embodiment, a full length scFvFc: ζ cDNA, designated CE7R, comprises the human GM-CSF receptor alpha chain leader peptide, CE7 $V_H$, Gly-Ser linker, CE7 $V_L$, human IgG$_1$ Fc, human CD4 TM, and human cytoplasmic zeta chain. "Chimeric TCR" means a receptor which is expressed by T cells and which comprises intracellular signaling, transmembrane and extracellular domains, where the extracellular domain is capable of specifically binding in an HLA unrestricted manner an antigen which is not normally bound by a T cell receptor in that manner. Stimulation of the T cells by the antigen under proper conditions results in proliferation (expansion) of the cells and/or production of cytokines (e.g., IL-2) and/or cytolysis.

In a second aspect, the present invention provides a method of treating a CE7+ malignancy in a mammal which comprises administering CE7-specific redirected T cells to the mammal in a therapeutically effective amount. In one embodiment of this aspect of the invention, a therapeutically effective amount of CD8+ CE7-specific redirected T cells are administered to the mammal. The CD8+ T cells are preferably administered with CD4+ CE7-specific redirected T cells. In a second embodiment of this aspect of the invention, a therapeutically effective amount of CD4+ CE7-specific redirected T cells are administered to the mammal. The CD4+ T cells are preferably administered with CD8+ T CE7-specific redirected T cells.

In a third aspect, the present invention provides a method of making and expanding the CE7-specific redirected T cells which comprises transfecting T cells with an expression vector containing a DNA construct encoding the CE7-specific chimeric receptor, then stimulating the cells with CE7+ cells, recombinant CE7, or an antibody to the receptor to cause the cells to proliferate. According to this aspect of the present invention, the method preferably stably transfects and re-directs T cells using electroporation of naked DNA. Alternatively, viral vectors carrying the heterologous genes are used to introduce the genes into T cells. By using naked DNA, the time required to produce redirected T cells can be significantly reduced. "Naked DNA" means DNA encoding a chimeric T cell receptor (TCR) contained in an expression cassette which comprises the structural gene for the chimeric T cell receptor to which is attached regulatory DNA regions (promoter, enhancer, polyadenylkation site and the like) that permit expression of the gene in transfected cells. The naked DNA may further be covalently bound to plasmid DNA as a DNA delivery or expression vector. The electroporation method of this invention produces stable transfectants which express and carry on their surfaces the chimeric TCR (cTCR).

In a preferred embodiment of the transfection method of the invention, the T cells are primary human T cells, such as human peripheral blood mononuclear cells (PBMC), which have previously been considered resistant to stable transfection by electroporation of plasmid vectors. Preferred conditions include the use of DNA depleted of endotoxin and electroporation within about 3 days following mitogenic stimulation of T cells. Following transfection, the transfectants are cloned and a clone demonstrating presence of a single integrated unrearranged plasmid and expression of the chimeric receptor is expanded ex vivo. The clone selected for expansion preferably is CD8+ and demonstrates the capacity to specifically recognize and lyse neuroblastoma target cells which express the target epitope of CE7. The clone is expanded by stimulation with IL-2 and preferably another stimulant which is specific for the cTCR.

The invention is described herein primarily with reference to the specific scFvFc: ζ construct and receptor of SEQ ID NOs:1 and 2, but the invention is not limited to that specific construct and receptor. The scFv portion can be replaced by any number of different CE7 binding domains, ranging from a minimal peptide binding domain, to a structured CE7 binding domain from a phage library, to antibody like domains using different methods to hold the heavy and light chain (or peptide-binding domains of each) together. The arrangement could be multimeric such as a diabody. It is possible that the T cell receptor variant is also a multimer. Multimers are most likely caused by cross pairing of the variable portion of the light and heavy chains into what has been referred to by Winters as a diabody.

The hinge portion of the construct can have multiple alternatives from being totally deleted, to having the first cysteine maintained, to a proline rather than a serine substitution, to being truncated up to the first cysteine. The Fc portion of IgG$_1$ can be deleted or replaced with the Fc portion of IgG$_4$, although there is data to suggest that the receptor preferably extends from the membrane. Any protein which is stable and dimerizes can serve this purpose. One could use just one of the Fc domains, e.g., either the $C_H2$ or $C_H3$ domain.

Alternatives to the CD4 transmembrane domain include the transmembrane CD3 zeta domain, or a cysteine mutated CD3 zeta domain, or other transmembrane domains from other transmembrane signaling proteins such as CD16 and CD8. The CD3 zeta intracellular domain was taken for activation. Intracellular signaling portions of other members of the families of activating proteins can be used, such as FcγRIII and FcεRI. See Gross et al. [78], Stancovski et al. [68], Moritz et al. [70], Hwu et al. [79], Weijtens et al. [74], and Hekele et al. [71], for disclosures of cTCR's using these alternative transmembrane and intracellular domains.

Additional cytoplasmic domains which are known to augment lytic activity are contemplated by the present invention. Such additional cytoplasmic domains may be selected from the group including CD28 and 4-1BB. The cytoplasmic domains may be used together on a chimeric immune receptor arranged in "molecular series" or alternatively as distinct scFvFc constructs co-expressed on a redirected immune cell.

Cellular Immunotherapy Using Redirected T Cells

The strategy of isolating and expanding antigen-specific T cells as a therapeutic intervention for human disease has been validated in clinical trials [59, 80, 81]. Initial studies have evaluated the utility of adoptive T cell therapy with CD8+ cytolytic T cell (CTL) clones specific for cytomegalovirus-encoded antigens as a means of reconstituting deficient viral immunity in the setting of allogeneic bone marrow transplantation and have defined the principles and methodologies for T cell isolation, cloning, expansion and re-infusion [80]. A similar approach has been taken for controlling post-transplant EBV-associated lymphoproliferative disease. EBV-specific donor-derived T cells have the capacity to protect patients at high risk for this complication as well as eradicate clinically evident disease which mimics immunoblastic B cell lymphoma [81]. These studies clearly demonstrate that adoptively transferred ex vivo expanded T cells can mediate antigen-specific effector functions with minimal toxicities and have been facilitated by targeting defined virally-encoded antigens to which T cell donors have established immunity.

The application of adoptive T cell therapy as a treatment modality for human malignancy has been limited by the paucity of molecularly-defined tumor antigens capable of eliciting a T cell response and the difficulty of isolating these T cells from the tumor-bearing host. Consequently, initial cellular immunotherapy trials utilizing autologous antitumor effector cells relied on antigen nonspecific effector cells such as lymphokine activated killer (LAK) cells which had limited efficacy and pronounced toxicities [82, 83]. In an attempt to enhance the tumor-specificity of infused effector cells, IL-2 expanded tumor-infiltrating lymphocytes (TIL) were evaluated [84]. Responses to TIL infusions were sporadic due in part to the heterogeneous population of cells expanded with unpredictable antitumor specificities.

Patients with melanoma and renal cell carcinoma however occasionally manifested striking tumor regressions following TIL infusions and tumor-specific MHC-restricted T cell clones have been isolated from these patients. Recently, expression cloning technologies have been developed to identify the genes encoding tumor antigens thereby facilitating the development of recombinant DNA-based vaccine strategies to initiate or augment host antitumor immunity, as well as in vitro culture systems for generating tumor-specific T cells from cancer patients [85]. Clinical trials utilizing autologous tyrosinase-specific CTL for the treatment of melanoma are currently underway and will likely provide major insights into the efficacy of targeting tumors with antigen-specific MHC-restricted T cell clones.

Endowing T cells with a desired antigen specificity based on genetic modification with engineered receptor constructs is an attractive strategy since it bypasses the requirement for retrieving antigen-specific T cells from cancer patients and, depending on the type of antigen recognition moiety, allows for targeting tumor cell-surface epitopes not available to endogenous T cell receptors. Studies to define the signaling function of individual components of the TCR-CD3 complex revealed that chimeric molecules with intracellular domains of the CD3 complex's zeta chain coupled to extracellular domains which could be crosslinked by antibodies were capable of triggering biochemical as well as functional activation events in T cell hybridomas [86]. Recent advances in protein engineering have provided methodologies to assemble single chain molecules consisting of antibody variable regions connected by a flexible peptide linker which recapitulate the specificity of the parental antibody [87, 88]. Several groups have now reported on the capacity of chimeric single chain receptors consisting of an extracellular scFv and intracellular zeta domain to re-direct T cell specificity to tumor cells expressing the antibody's target epitope; receptor specificities have included HER2/Neu, and less well characterized epitopes on renal cell and ovarian carcinoma [68, 70, 71, 74, 78, 79]. An idiotype-specific scFv chimeric TCR has been described which recognizes the idiotype-expressing lymphoma cell's surface immunoglobulin as its ligand [78]. Although this approach swaps a low affinity MHC-restricted TRC complex for a high affinity MHC-unrestricted molecular linked to an isolated member of the CD3 complex, these receptors do activate T cell effector functions in primary human T cells without apparent induction of subsequent anergy or apoptosis [74]. Murine model systems utilizing scFvcζ transfected CTL demonstrate that tumor elimination only occurs in vivo if both cells and IL-2 are administered, suggesting that in addition to activation of effector function, signaling through the chimeric receptor is sufficient for T cell recycling [71].

Although chimeric receptor re-directed T cell effector function has been documented in the literature for over a decade, the clinical application of this technology for cancer therapy is only now beginning to be applied. ex vivo expansion of genetically modified T cells to numbers sufficient for re-infusion is required for conducting clinical trials. Not only have sufficient cell numbers been difficult to achieve, the retention of effector function following ex vivo expansion has not been routinely documented in the literature.

Treatment of $CE7^+$ Malignancies with CE7-Specific Redirected T Cells

This invention represents the targeting of a universal neuroblastoma cell-surface epitope with CE7-specific redirected T cells. Neuroblastoma cells are an excellent target for redirected T cells, as they express the CE7 target epitope antigen. CE7 target epitope is an ideal target epitope for recognition by CE7-specific redirected T cells due to the prevalence of $CE7^+$ disease, the uniformity of expression by tumor cells, and the stability of the CE7 target epitope molecule on the cell surface.

We have found that expansion of CE7 specific re-directed $CD8^+$ CTL clones with OKT3 and IL-2 routinely results in the generation of greater than $10^9$ cells over a period of approximately six weeks, and that the clones retain their effector function following expansion, as shown by functional chromium release assay data. Our observation that the plasmid/scFvFc: ζ system can generate transfectants with disrupted plasmid sequence underscores the desirability of cloning transfectants and expanding those clones demonstrating the presence of a single unrearranged integrated plasmid, expression of the chimeric receptor, and the capacity to specifically recognize and lyse $CE7^+$ neuroblastoma target cells.

Equipping T cells with a suicide gene such as the herpes virus thymidine kinase gene allows for in vivo ablation of transferred cells following adoptive transfer with pharmacologic doses of gancyclovir and is a strategy for limiting the duration or in vivo persistence of transferred cells [89].

Patients can be treated by infusing therapeutically effective doses of $CD8^+$ CE7-specific redirected T cells in the range of about $10^6$ to $10^{12}$ or more cells per square meter of body surface (cells/m²). The infusion will be repeated as often and as many times as the patient can tolerate until the desired response is achieved. The appropriate infusion dose and schedule will vary from patient to patient, but can be determined by the treating physician for a particular patient. Typically, initial doses of approximately $10^9$ cells/m² will be infused, escalating to $10^{10}$ or more cells/m². IL-2 can be co-administered to expand infused cells post-infusion. The amount of IL-2 can about $10^3$ to $10^6$ units per kilogram body weight. Alternatively or additionally, an scFvFc: ζ-expressing $CD4^+$ $T_{H1}$ clone can be co-transferred to optimize the survival and in vivo expansion of transferred scFvFc: ζ-expressing $CD8^+$ T cells.

The dosing schedule may be based on Dr. Rosenberg's published work [72-73] or an alternate continuous infusion strategy may be employed. CE7-specific redirected T cells can be administered as a strategy to support $CD8^+$ cells.

It is known that chimeric immune receptors are capable of activating target-specific lysis by phagocytes, such as neutrophils and NK cells, for example (90). Thus, the present invention also contemplates the use of chimeric T-cell receptor DNA to transfect into non-specific immune cells including neutrophils, macrophages and NK cells. Furthermore, the present invention contemplates the use of chimeric T-cell receptor DNA to transfect stem cells prior to stem cell transplantation procedures.

The practice of the present invention employs, unless otherwise indicated, conventional techniques of chemistry, molecular biology, microbiology, recombinant DNA, genetics, immunology, cell biology, cell culture and transgenic biology, which are within the skill of the art. [See, e.g., 91-108].

EXAMPLES

The present invention is further detailed in the following examples, which are offered by way of illustration and are not intended to limit the invention in any manner. Standard techniques well known in the art or the techniques specifically described below are utilized.

Example 1

Construction of a scFvFc: ζ cDNA Incorporating the CE7 $V_H$ and $V_L$ Sequences and Expression of the Construct in T-Cells Based on the sequences published by Amstutz et al., PCR was carried out on cDNA generated from the CE7 hybridoma and cloned $V_H$ and $V_L$ segments were isolated and sequenced [54]. Referring now to FIG. 2A, there is shown a schematic of the CE7R/scFvFc: ζ chimeric receptor. A full length scFvFc: ζ cDNA designated CE7R was constructed using method well known in the art by PCR splice overlap extension and consists of the human GM-CSF receptor alpha chain leader peptide, CE7 $V_H$, Gly-Ser linker, CE7 $V_L$, human $IgG_1$ Fc, human CD4 TM, and human cytoplasmic zeta chain. The amino acid sequence of the receptor is shown in SEQ ID NO:2.

Figure 2B:
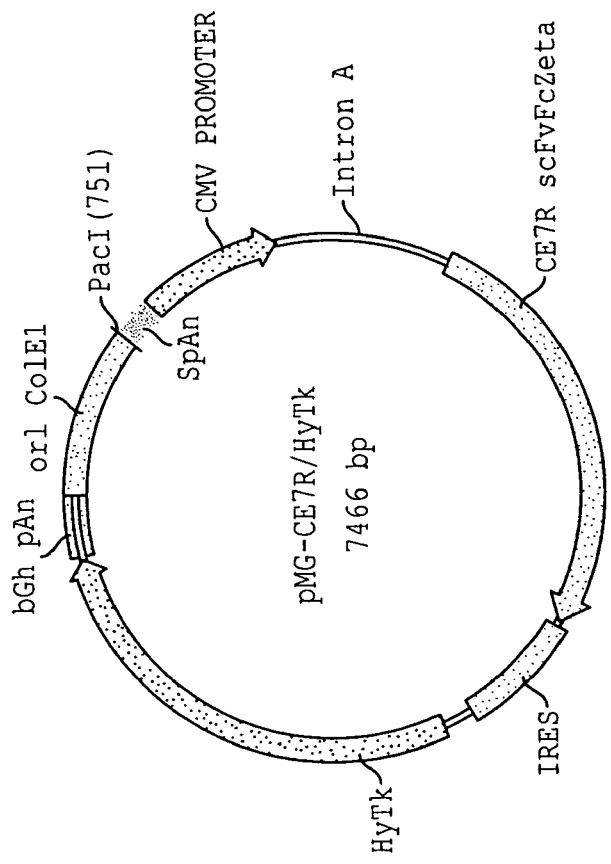
FIG. 2B is a schematic representation of the plasmid pMG-CE7R/HyTK; the sequence which is shown in FIG. 1 A-H.

Referring now to FIG. 2B, there is shown a plasmid comprising the CE7R/scFvFc: ζ chimeric receptor in an expression vector. Using methods well known in the art, the cDNA construct containing the CE7R/scFvFc: ζ chimeric receptor was ligated into the multiple cloning site of a modified pMG plasmid (Invitrogen, San Diego) to generate pMG-CE7R/HyTk. This expression vector co-expresses the HyTK cDNA encoding hygromycin phosphotransferase for in vitro drug selection and the herpes thymidine kinase that renders cells susceptible to the cytotoxic action of ganciclovir. Expression of the CE7R scFvFc: ζ and HyTK is linked by the dicistronic mRNA configuration having an internal ribosome entry site (IRES). The scFvFc: ζ cDNA is 5' to HyTK in pMG. "SpAn" represents a synthetic polyadenylation site with a strong pause site to limit transcriptional interference. The synthetic polyA site is based on the rabbit B-globin gene using a highly conserved AATAAA sequence and a GT/T rich flanking sequence downstream from the hexanucleotide sequence (109). The pause site is derived from the C2 complement gene (110). The symbol "bGh pAn" represents the bovine growth hormone (bGh) polyadenylation (pAn) signal and a transcriptional pause site (111). It is used to minimize interference and possible recombination events. The nucleotide sequence of this plasmid is shown in SEQ ID NO:5 and FIG. 1A-H.

Figure 3:
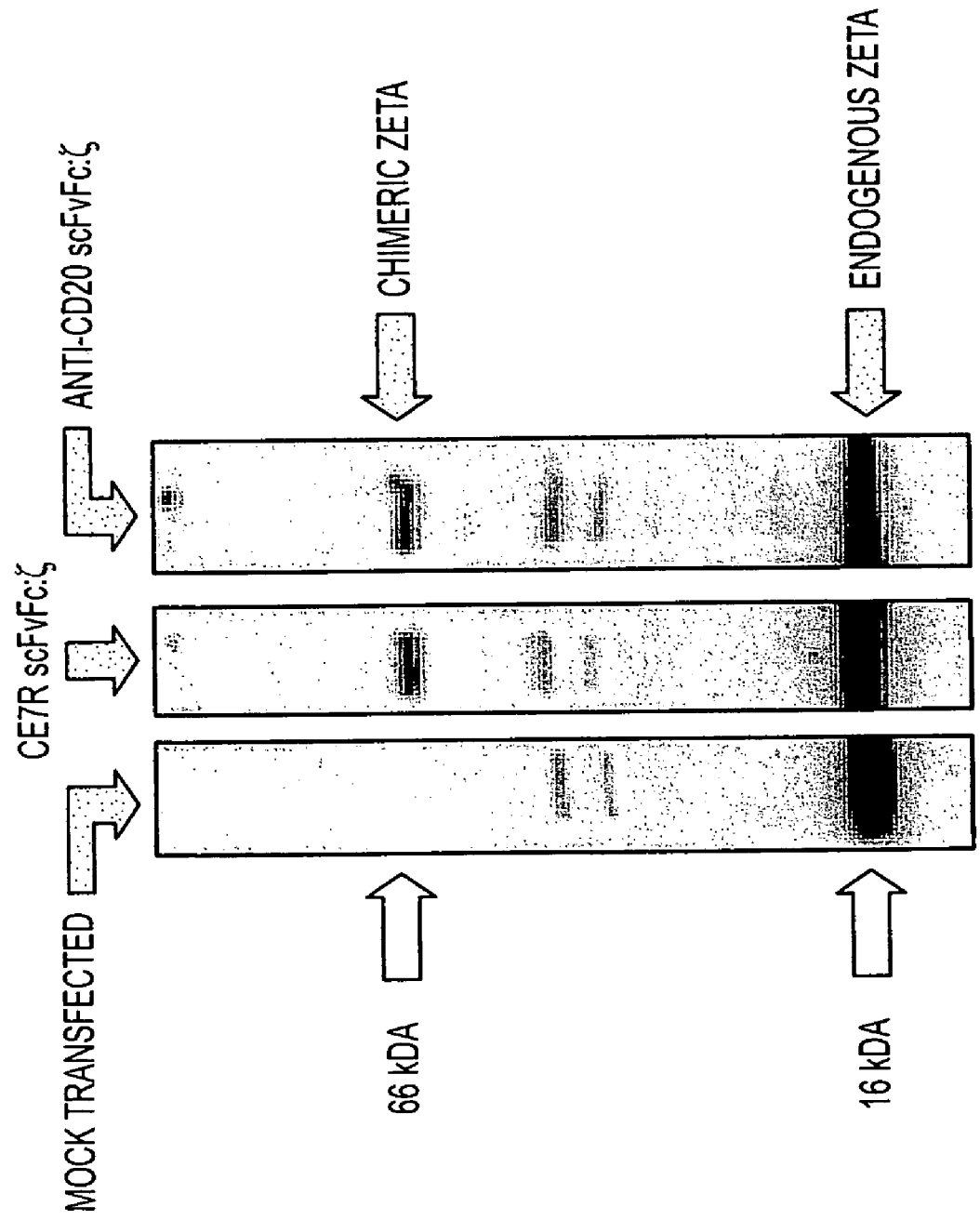
FIG. 3 shows Western blot analyses which demonstrate the expression of the CE7R/scFvFc: ζ chimeric receptor.

The CE7-specific scFvFc: ζ receptor protein is expressed in Primary Human T cells. To determine whether the CE7-specific scFvFc: ζ construct could be expressed as an intact chimeric protein, T cells were transfected with the plasmid of Example 1 containing the CE7 Chimeric receptor. Linearized plasmid was electroporated under optimized conditions and stable transfectants selected by addition of hygromycin to cultures. Referring now to FIG. 3, there are shown the results of Western blot analyses of T-cells transfected with the CE7R/scFvFc: ζ chimeric receptor in an expression vector of the present invention. Using methods known in the art, whole cell lysates from mock transfectants (cells containing the pMG plasmid without the CE7R/scFvFc: ζ chimeric receptor), T-cells transfected with the CE7R/scFvFc: ζ chimeric receptor, and T-cells transfected with another chimeric receptor (Anti CD20 scFvFc: ζ) were examined. Western blot of whole cell lysates with an anti-zeta antibody probe shows both the endogenous zeta fragment and the expected intact 66-kDa chimeric receptor protein is expressed in cells transfected with a chimeric receptor but not in cells transfected with plasmid lacking the DNA constructs of the present invention.

Figure 4B:
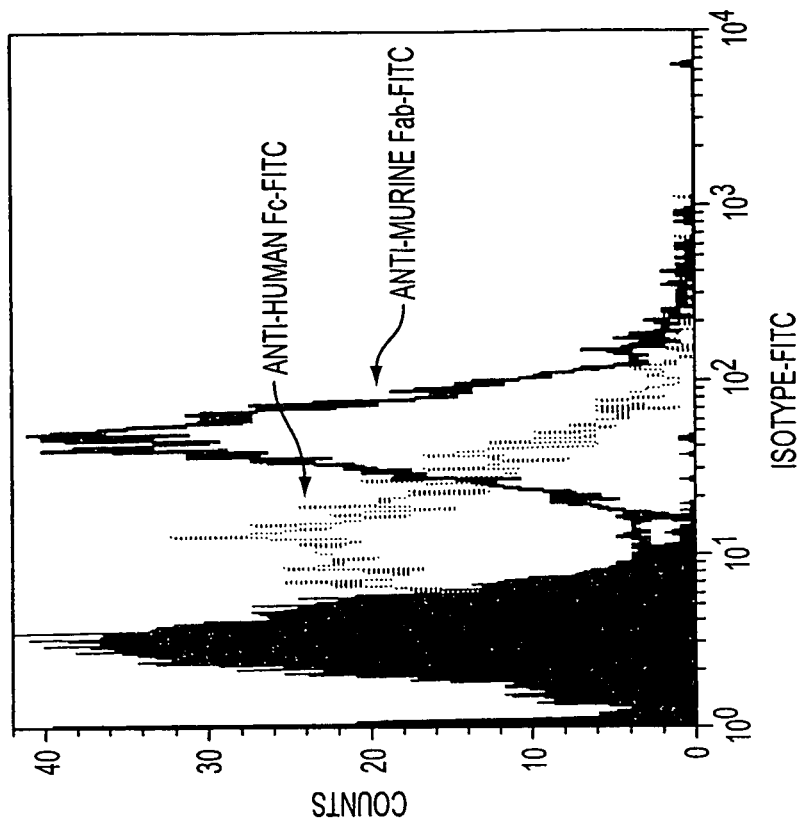
FIGS. 4A and 4B show the results of Fluorescent Activated Cell Sorting which demonstrate the cell surface location of the CE7R/scFvFc: ζ chimeric receptor. Flow cytometric analysis of transfected T-cells reacted with anti-murine FAB which react with the CE7 portion of the CE7R and anti-human Fc specific antibodies which react with the IgG portion of the CE7R, confirmed the cell-surface expression of the CE7R scFvFc: ζ on T cell transfectants (FIG. 4B) as evidenced by cosegregation of the CE7R antigens with known T cell antigens (FIG. 4A).
Figure 4A:
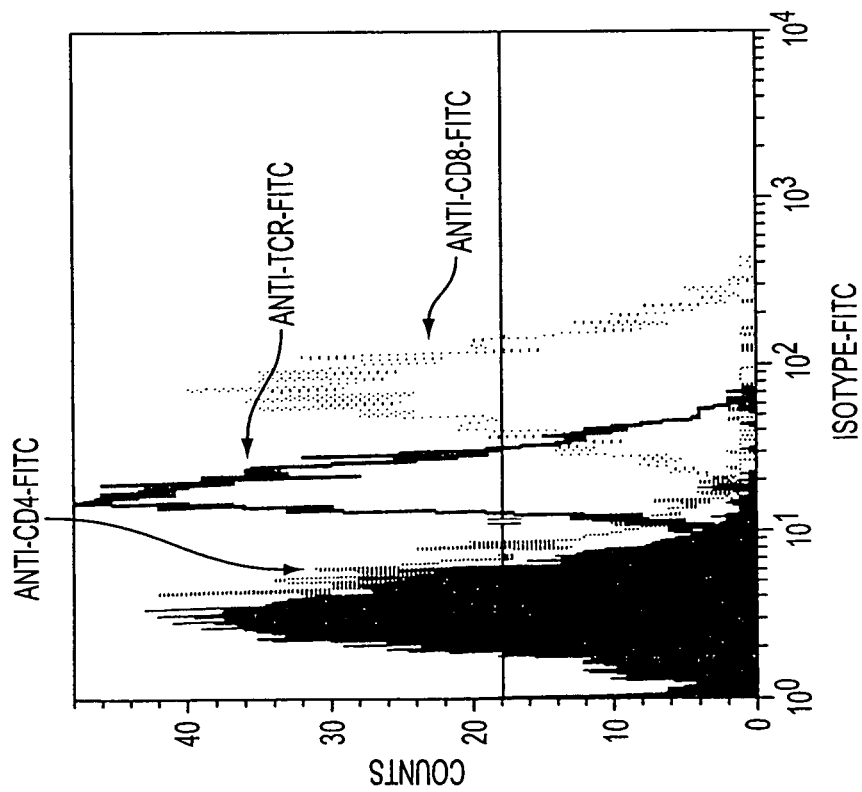

Referring now to FIG. 4, there are shown the results of flow cytometric analysis of the transfected cells of the present invention. Using methods known in the art and discussed in detail in the following Examples, flow cytometric analysis of transfected T-cells reacted with anti-murine FAB which react with the CE7 portion of the CE7R and anti-human Fc specific antibodies which react with the IgG portion of the CE7R, confirmed the cell-surface expression of the CE7R scFvFc: ζ on T cell transfectants as evidenced by cosegregation of the CE7R antigens with known T cell antigens.

Example 2

Figure 5:
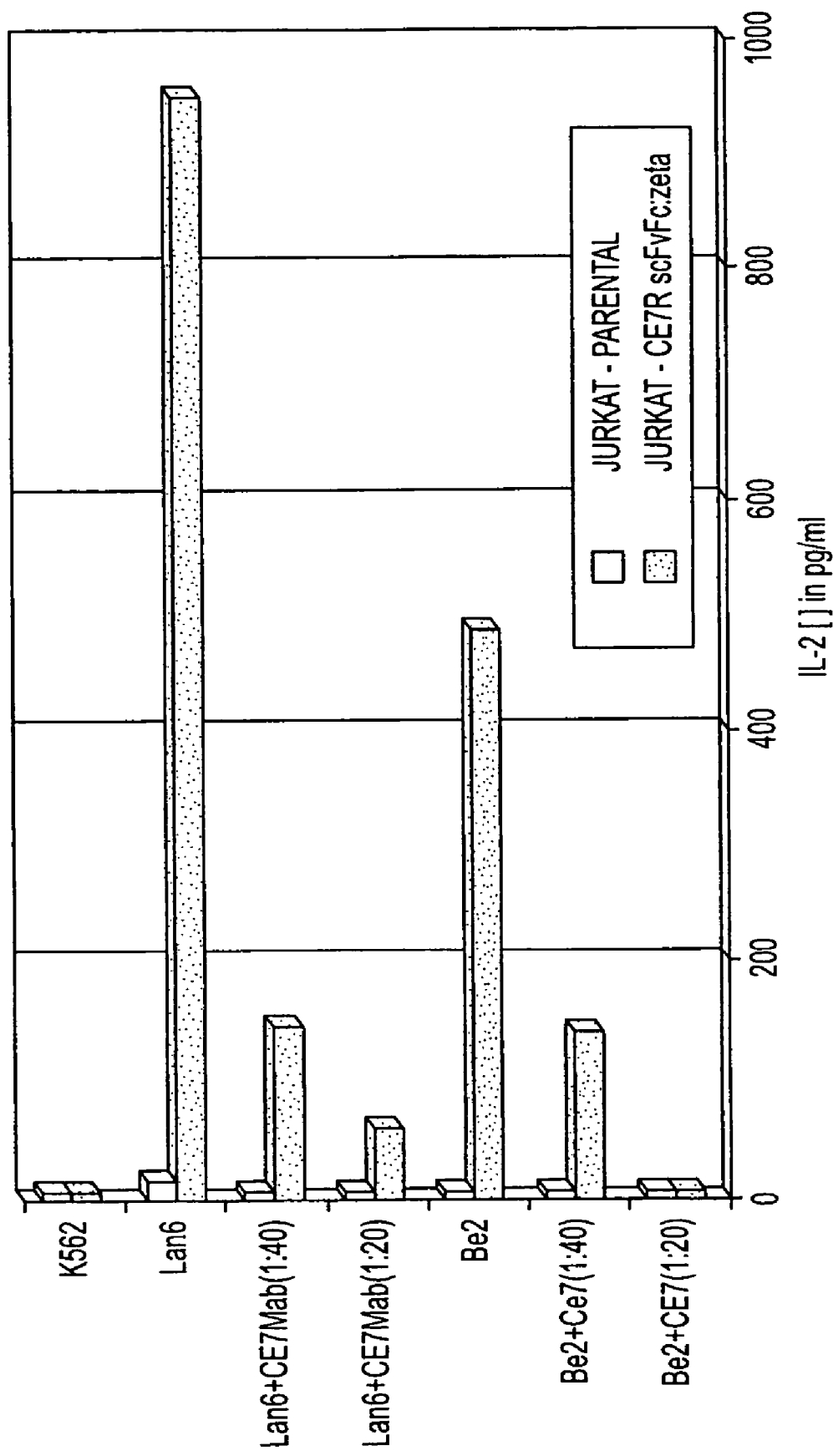
FIG. 5 is a graphical representation which shows the production of IL-2 by Jurkat T-cells expressing the CE7R/scFvFc: ζ chimeric receptor that are co-cultured with neuroblastoma cells.
Figure 6A:
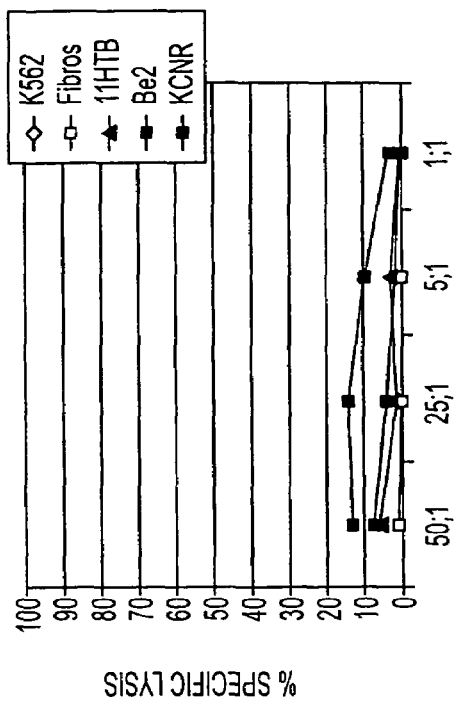
FIG. 6 A-D are graphical representations showing the anti-neuroblastoma activity of primary human CD8+ cytotoxic T lymphocytes expressing the CE7R/scFvFc: ζ chimeric receptor.
Figure 6C:
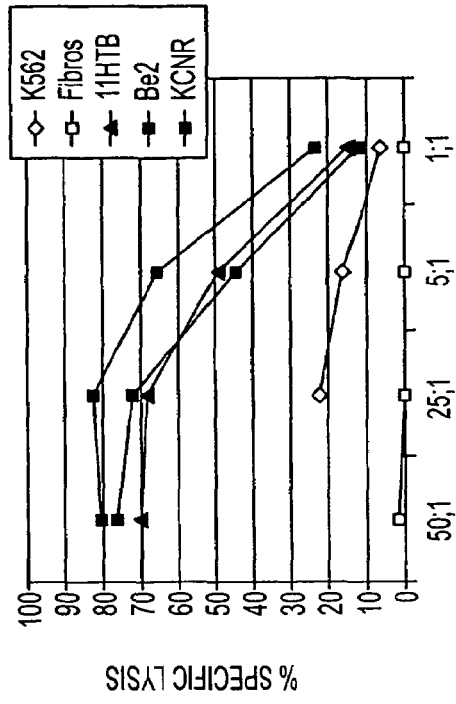
Figure 6B:
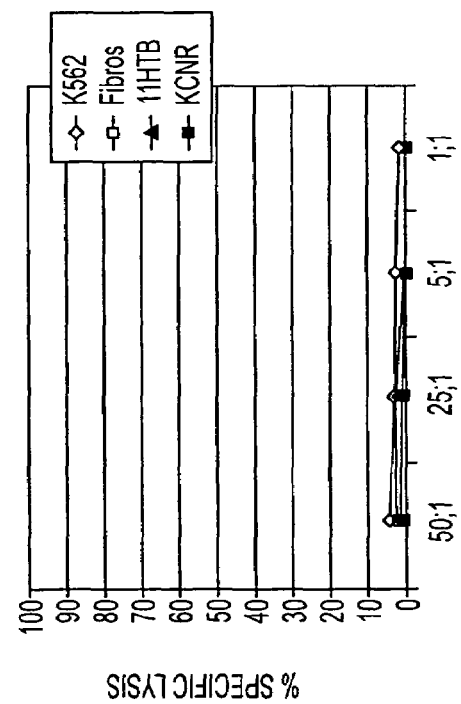
Figure 6D:
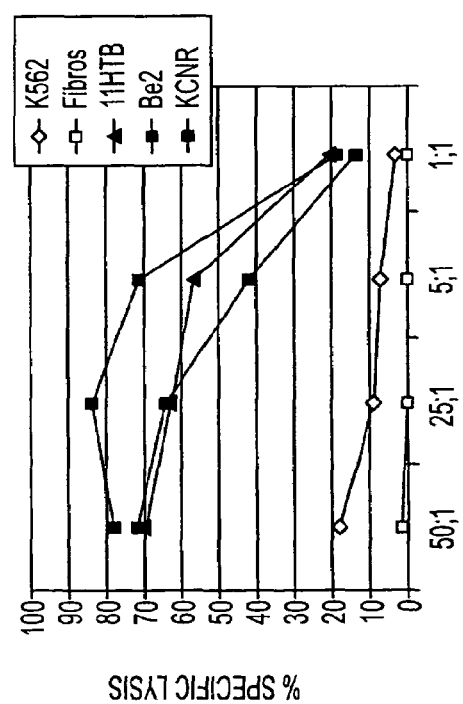

Anti-Neuroblastoma Effector Functions of T Cells Expressing the CE7R Chimeric Immunoreceptor IL-2 Production Referring now to FIG. 5, there is a graphical representation which shows the production of IL-2 by T-cells expressing the CE7R/scFvFc: ζ chimeric receptor that are co-cultured with neuroblastoma cells. Using techniques known to those skilled in the art and discussed in detail in the following examples, the function of the CE7R chimeric immunoreceptor in T cells was first assessed by expressing this scFvFc: ζ construct in Jurkat T cells. CE7R+ Jurkat transfectants produced IL-2 when co-cultured with a panel of neuroblastoma cell lines. IL-2 production was antigen specific as evidenced by the observations that mock transfected Jurkat cells are not activated to produce IL-2 when exposed to the same neuroblastoma stimulators and that IL-2 production was inhibited in a dose-dependent fashion by the addition to culture of soluble CE7 mAb.

Cytotolytic Activity

Referring now to FIGS. 6 A-D, there are shown graphical representations the anti-neuroblastoma activity of $CD8^+$ cells expressing the CE7R/scFvFc: ζ chimeric receptor. Primary human $CD4^+$ and $CD8^+$ T cell clone transfectants expressing the CE7R have been generated using techniques well known in the art and discussed further in detail in the following Examples. Like Jurkat transfectants, $CD4^+$ and $CD8^+$ clones secrete cytokines (IFN-γ and gm-CSF) specifically upon co-culture with human neuroblastoma cells. Moreover, $CE7R^+$ $CD8^+CTL$ clones display high levels of cytolytic activity in standard 4-hr chromium release assays against human neuroblastoma cell lines yet do not kill primary human fibroblasts ("Fibros" in FIG. 6) or other tumor lines that are devoid of the CE7 epitope ("K562" in FIG. 6).

Example 3

Generation and Characterization of T Cell Clones for Therapeutic Use

All T cells administered are TCR a/b$^+$ $CD4^-CD8^+$ scFvFc: ζ$^+$ T cell clones containing unrearranged chromosomally integrated plasmid DNA. T cells are isolated from the peripheral blood of patient's with recurrent/refractory neuroblastoma. Materials and methods employed to isolate, genetically modify, and expand $CD8^+$ T cell clones from healthy marrow donors are detailed in Examples 4-8. T cell clones genetically modified to express the CE7R scFvFc: ζ chimeric immunoreceptor and HyTK are selected for:

a. TCRa/b$^+$, CD4$^-$, CD8$^+$ surface phenotype as determined by flow cytometry.
b. Presence of a single copy of chromosomally integrated plasmid vector DNA as evidenced by Southern blot.
c. Expression of the scFvFc: ζ gene product as detected by Western blot.
d. Specific lysis of human CE7$^+$ cell lines in 4-hr chromium release assays.
e. Dependence on exogenous IL-2 for in vitro growth.
f. Mycoplasma, fungal, bacterial sterility and endotoxin levels <5 EU/ml.
g. In vitro sensitivity of clones to ganciclovir.

Example 4

Materials for Isolating, Genetically Modifying and Expanding CD8$^+$ T Cell Clones from Healthy Marrow Donors for Therapeutic Use 1. Culture Media and Media Supplements Culture media used in the studies include RPMI 1640 HEPES (Irvine Scientific, Irvine, Calif.) for all cell cultures. All media is purchased in 0.5 liter bottles and meets current FDA guidelines for use in adoptive immunotherapy studies in humans. Supplements to the culture media include L-glutamine (BioWhittaker, Walkersville, Md.) and fetal calf serum (Hyclone, Logan, Utah) heat inactivated at 56° C. for 30 minutes. All reagents are shipped to CRB-3008, inspected, and stored at −20° C. or 4° C. as appropriate for the reagent.

2. OKT3

Orthoclone OKT3 (Ortho) 1 mg/ml is aliquoted into sterile cryovials are stored at −20° C. in CRB-3008 until thawed for study subject T cell expansion.

3. Interleukin 2

Pharmaceutical grade recombinant human Interleukin-2 (rhIL-2) (Proleukin, Chiron, Emeryville, Calif.) is supplied in vials containing 0.67 mg of lyophilized IL-2 and having a specific activity of 1.5×10$^6$ IU/mg protein. The lyophilized recombinant IL-2 is reconstituted with sterile water for infusion and diluted to a concentration of 5×10$^4$ units/ml. IL-2 is aliquoted into sterile vials and stored at −20° C. in CRB-3008. rhIL-2 for direct patient administration is dispensed per standard practice.

4. Plasmid DNA

The plasmid pMG-CE7R/HyTK containing the CE7-specific scFvFc: ζ cDNA and HyTK cDNA constructs is manufactured under GLP conditions Ampules containing 100 mg of sterile plasmid DNA in 40 ml of pharmaceutical water. Vector DNA is stored in a −70° C. freezer in CRB-3008.

5. Hygromicin

The mammalian antibiotic hygromycin is used to select genetically modified T cells expressing the HyTK gene. Commercially available hygromycin (Invitrogen, San Diego, Calif.) is prepared as a sterile solution of 100 mg/ml active drug and is stored at 4° C. in CRB-3008.

6. EBV-Induced B Cell Lines

Lymphoblastoid cell lines (LCL) are necessary feeder cells for T cell expansion and have been used for this purpose in FDA-approved clinical adoptive therapy trials. An EBV-induced B cell line designated TM-LCL was established from a healthy donor by co-culture of PBMC with supernatants of the B95-8 cell line (American Type Culture Collections) in the presence of cyclosporin A. This cell line is used as an irradiated feeder cell line. This cell line has tested negative for adventitious microorganisms as well as EBV production by cord blood transformation assay. Working stocks of TM-LCL have been cyropreserved in CRB-3008 after transfer. These stocks have been thawed and retested for bacterial, fungal and mycoplasma sterility. TM-LCL feeder cells are irradiated to 8,000 cGy prior to co-culture with T cells.

7. Feeder PBMCs

Allogeneic PBMC isolated from healthy donors meeting Blood Bank criteria and laboratory screening for clinical cell product donation are harvested by leukapheresis and supplied to CRB 3008 in a collection bag following irradiation to 3,300 cGy. This apheresis product is then cyropreserved in ampules containing 50×10$^6$ mononuclear cells in the CRB-3008 liquid nitrogen tank.

Example 5

Generation of CD8$^+$ CTL Clones Genetically Modified to Express the CE7-Specific scFvFc: ζ Receptor (CE7R) and HyTK 1. Peripheral Blood Lymphocytes—Collection and Separation Peripheral blood mononuclear cells (PBMC) are obtained from the study subject's designated marrow donor by leukapheresis. The mononuclear cells are separated from heparinized whole blood by centrifugation over clinical grade Ficoll (Pharmacia, Uppsula, Sweden). PBMC are washed twice in sterile phosphate buffered saline (Irvine Scientific) and suspended in culture media consisting of RPMI, 10% heat inactivated FCS, and 4 mM L-glutamine.

2. Activation of PBMC

T cells present in patient PBMC are polyclonally activated by addition to culture of Orthoclone OKT3 (30 ng/ml). Cell cultures are then incubated in vented T75 tissue culture flasks in the study subject's designated incubator. Twenty-four hours after initiation of culture rhIL-2 is added at 25 U/ml.

3. Genetic Modification of Activated PBMC

Three days after the initiation of culture PBMC are harvested, centrifuged, and resuspended in hypotonic electroporation buffer (Eppendorf) at 20×10$^6$ cells/ml. 25 mg of plasmid DNA together with 400 ml of cell suspension are added to a sterile 0.2 cm electroporation cuvette. Each cuvette is subjected to a single electrical pulse of 250V/40 ms delivered by the Multiporator (Eppendorf) then incubated for ten minutes at room temperature. Following the RT incubation, cells are harvested from cuvettes, pooled, and resuspended in phenol red-free culture media containing 25 U/ml rhIL-2. Flasks are placed in the patient's designated tissue culture incubator. Three days following electroporation hygromycin is added to cells at a final concentration of 0.2 mg/ml. Electroporated PBMC are cultured for a total of 14 days with media and IL-2 supplementation every 48-hours.

4. Cloning of Hygromycin-Resistant T Cells

The cloning of hygromycin-resistant CD8$^+$CTL from electroporated OKT3-activated patient PBMC is initiated on day 14 of culture. Cells expressing FvFc product are positively selected for using antibodies to Fab and Fc and/or Protein A-FITC label using techniques well known in the art. Following incubation of electroporated cells with Fab and Fc antibody or Protein A-FITZ, cells expressing the FvFc are isolated by immunogenetic beads or columnmns or fluorescent activated cel sorting procedures. Viable patient PBMC are added to a mixture of 100×10$^6$ cyropreserved irradiated feeder PBMC and 20×10$^6$ irradiated TM-LCL in a volume of 200 ml of culture media containing 30 ng/ml OKT3 and 50

U/ml rhIL-2. This mastermix is plated into ten 96-well cloning plates with each well receiving 0.2 ml. Plates are wrapped in aluminum foil to decrease evaporative loss and placed in the patient's designated tissue culture incubator. On day 19 of culture each well receives hygromycin for a final concentration of 0.2 mg/ml. Wells are inspected for cellular outgrowth by visualization on an inverted microscope at Day 30 and positive wells are marked for restimulation.

5. Expansion of Hygromycin-Resistant Clones with CE7 Re-Directed Cytotoxicity

The contents of each cloning well with cell growth and cytolytic activity by screening chromium release assay are individually transferred to T25 flasks containing $50 \times 10^6$ irradiated PBMC, $10 \times 10^6$ irradiated LCL, and 30 ng/ml OKT3 in 25 mls of tissue culture media. On days 1, 3, 5, 7, 9, 11, and 13 after restimulation flasks receive 50 U/ml rhIL-2 and 15 mls of fresh media. On day 5 of the stimulation cycle flasks are also supplemented with hygromycin 0.2 mg/ml. Fourteen days after seeding cells are harvested, counted, and restimulated in T75 flasks containing $150 \times 10^6$ irradiated PBMC, $30 \times 10^6$ irradiated TM-LCL and 30 ng/ml OKT3 in 50 mls of tissue culture media. Flasks receive additions to culture of rhIL-2 and hygromycin as outlined above.

6. Characterization of Hygromycin-Resistant CTL Clones a. Cell Surface Phenotype CTL selected for expansion for use in therapy are analyzed by immunofluorescence on a FACSCalibur housed in CRB-3006 using FITC-conjugated monoclonal antibodies WT/31 (αβTCR), Leu 2a (CD8), and OKT4 (CD4) to confirm the requisite phenotype of clones (abTCR$^+$, CD4$^-$, and CD8$^+$). Criteria for selection of clones for clinical use include uniform TCR ab$^+$, CD4$^-$, CD8$^+$ as compared to isotype control FITC-conjugated antibody.

b. Chromosomal Integration of Plasmid

A single site of plasmid vector chromosomal integration was confirmed by Southern blot analysis. DNA from genetically modified T cell clones was screened with a DNA probe specific for the plasmid vector. The HyTK-specific DNA probe was the 420 basepair MscI/NaeI restriction fragment isolated from pMG-CE7R/HyTK. Probe DNA was $^{32}$p labeled using a random primer labeling kit (Boehringer Mannheim, Indianapolis, Ind.). T cell genomic DNA was isolated per standard technique. Ten micrograms of genomic DNA from T cell clones was digested overnight at 37° C. with 40 units of XbaI and HindIII and then electrophoretically separated on a 0.85% agarose gel. DNA was then transferred to nylon filters (BioRad, Hercules, Calif.) using an alkaline capillary transfer method. Filters were hybridized overnight with the HyTK-specific $^{32}$P-labeled probe in 0.5 M Na$_2$PO$_4$, pH 7.2, 7% SDS, containing 10 µg/ml salmon sperm DNA (Sigma) at 65° C. Filters were then washed four times in 40 mM Na$_2$PO$_4$, pH 7.2, 1% SDS at 65° C. and then visualized using a phosphoimager (Molecular Dynamics, Sunnyvale, Calif.). Criteria for clone selection is a single unique band with the HyTK probe.

c. Expression of the CE7-Specific scFvFc: ζ Receptor

Expression of the CE7R scFvFc: ζ receptor is determined by Western blot procedure in which chimeric receptor protein is detected with an anti-zeta antibody. Whole cell lysates of transfected T cell clones were generated by lysis of $2 \times 10_7$ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim). After an eighty minute incubation on ice, aliquots of centrifuged whole cell lysate supernatant were harvested and boiled in an equal volume of loading buffer under reducing conditions then subjected to SDS-PAGE electrophoresis on a precast 12% acrylamide gel (BioRad). Following transfer to nitrocellulose, membranes were blocked in blotto solution containing 0.07 gm/ml non-fat dried milk for 2 hours. Membranes were washed in T-TBS (0.05% Tween 20 in Tris buffered saline pH 8.0) then incubated with primary mouse anti-human CD3ζ monoclonal antibody 8D3 (Pharmingen, San Diego, Calif.) at a concentration of 1 mg/ml for 2 hours. Following an additional four washes in T-TBS, membranes are incubated with a 1:500 dilution of goat anti-mouse IgG alkaline phosphatase-conjugated secondary antibody for 1 hour. Prior to developing, membranes were rinsed in T-TBS then developed with 30 ml of "AKP" solution (Promega, Madison, Wis.) per the manufacturer's instructions. Criteria for clone selection is the presence of a 66 kDa chimeric zeta band.

d. Cytolytic Specificity for CE7+ Cells and Lack of Cytolytic Activity Against Recipient Fibroblasts Activity CD8$^+$ cytotoxic T cell clones expressing the CE7R scFvFc: ζ receptor recognize and lyse human CE7$^+$ target cells following interaction of the chimeric receptor with the cell surface target epitope in an HLA unrestricted fashion. The requirements for target cell CE7 expression and class IMHC independent recognition are confirmed by assaying each αβTCR$^+$, CD8$^+$, CD4$^-$, CE7R$^+$ CTL clones against a panel of MHC-mismatched human neuroblastoma cell lines (KCNR, Be-2) as well as the CE7$^-$ line K562 (a CE7-negative, NK-sensitive target) and recipient fibroblasts. T cell effectors are assayed 12-14 days following stimulation with OKT3. Effectors are harvested, washed, and resuspended in assay media; $2.5 \times 10^5$, $1.25 \times 10^5$, $0.25 \times 10^5$, and $0.05 \times 10^3$ effectors are plated in triplicate at 37° C. for 4 hours with $5 \times 10^3$ target cells in V-bottom microtiter plates (Costar, Cambridge, Mass.). After centrifugation and incubation, 100 mL aliquots of cell-free supernatant is harvested and counted. Percent specific cytolysis is calculated as follows:

$$\frac{(\text{Experimental } ^{51}Cr \text{ release}) - (\text{control } ^{51}Cr \text{ release})}{(\text{Maximum } ^{51}Cr \text{ release}) - (\text{control } ^{51}Cr \text{ release})} \times 100$$

Control wells contain target cells incubated in assay media. Maximum $^{51}$Cr release is determined by measuring the $^{51}$Cr content of target cells lysed with 2% SDS. Criteria for clone selection is >50% specific lysis of both neuroblastoma targets at an effector:target ratio of 25:1 and less than 10% specific lysis of K562 and fibroblasts at an E:T ratio of 5:1.

Example 6

Microbiologic Surveillance of T Cell Cultures

Aliquots of media from the T cell cultures are plated onto bacterial and fungal growth media every 14 days. Cultures with evident contamination will be immediately discarded. To detect mycoplasma contamination, aliquots are assayed every 14 days using the Gen-Probe test kit (San Diego, Calif.) and cultures with mycoplasma contamination discarded. Prior to infusion of T cell clones and following resuspension in 0.9% saline, Gram staining will be done on the cell suspension to exclude overt contamination and endotoxin levels determined by ELISA to exclude cell product re-infusion if levels are above a 5 EU/kg burden of endotoxin is present in the cell product. T cell clones will also be cyropreserved in case archival specimens are needed.

Example 7

Quality Control Criteria for Release of Clones for Re-Infusion

The criteria set forth in Table 1 must be met prior to release of T cells for re-infusion.

TABLE 1

Criteria for Release of Clones

| Test for: | Release Criteria: | Testing Method: |
|---|---|---|
| Viability of Clinical Preparation | >90% | Trypan blue exclusion |
| Cell-Surface Phenotype | Uniformly TCRa/b$^+$, CD4$^+$, CD8$^+$ | Flow cytometric evaluation with isotype controls. |
| Vector Rearrangement | Single band | Southern Blot with HyTK-Specific Probe |
| scFvFc: ζ Expression | 66-kD Band | Western Blot with Human Zeta-Specific Primary Antibody |
| Anti-Neuroblastoma Cytolytic Activity | >50% Specific Lysis at E:T Ratio of 25:1 Against KCNR and Be-2 and <25% SL against K562 and fibros at an E:T of 5:1. | 4 hr-Chromium Release Assay |
| Sensitivity to Ganciclovir | <10% Cell viability After 14-days of co-culture in 5 μM ganciclovir. | Trypan blue-exclusion cell enumeration. |
| Sterility | All screening bacterial/fungal cultures neg for >7 days. Mycoplasma neg at time of cyropreservation and within 48 hrs of each infusion. Endotoxin level <5E.I./kg in washed cell preparation. Gram stain negative on day of re-infusion. | Bacterial/fungal by routine clinical specimen culture. Mycoplasma by Gene-Probe RIA. Endotoxin by ELISA. Gram stain by clinical microbiology lab. |

Example 8

Quantitative PCR for T Cell Persistence In Vivo

The duration of in vivo persistence of scFvFc:ζ CD8$^+$ CTL clones in the circulation is determined by quantitative PCR (Q-PCR) utilizing the recently developed TaqMan fluorogenic 5' nuclease reaction. Q-PCR analysis is performed by the Cellular and Molecular Correlative Core on genomic DNA extracted from study subject PBMC obtained prior to and on days +1 and +7 following each T cell infusion. Following the third infusion PBMC are also sampled on day +14, +21, +51 (Day +100 following stem cell rescue). Should any study subject have detectable gene-modified T cells on day +100, arrangements are made to re-evaluate the patient monthly until the signal is undetectable. Published data from Riddel et al. has determined that adoptively transferred T cells are detected in the peripheral blood of study subjects one day following a cell dose of $5 \times 10^9$ cells/m$^2$ at a frequency of 1-3 cells/100 PBMC, thus the doses of cells for this study will result in a readily detectable signal (77). DNA is extracted from PBMC using the Qiagen QiAmp kit. The primers used to detect the scFvFc: ζ gene are SEQ ID NO:6: 5'-TCTTCCTCTACA-CAGCAAGCT CACCGTGG-3'), the 5' heavy chain Fc specific primer, and SEQ ID NO:7: 5'-GAGGGTTCTTCCT TCCTTCTCGGCTTTC-3'), the 3' HuZeta primer, which amplify a 360 basepair fragment spanning the Fc-CD4-TM-zeta sequence fusion site. The TaqMan hybridization probe is SEQ ID NO:8: 5'-TTCACTCTGAA GAAGATGC-CTAGCC-3' that is 5'FAM—3'TAMRA labeled. A standard curve is generated from genomic DNA isolated from a T cell clone with a single copy of integrated plasmid spiked into unmodified T cells at frequencies of $10^{-2}$, $10^{-3}$, $10^{-4}$, $10^{-5}$, and $10^{-6}$. A control primer/probe set specific for the human beta-globin gene is used to generate a standard curve for cell number and permits the calculation of the frequency of genetically modified clone in a PBMC sample. The beta-globin amplimers are as follows: SEQ ID NO:9: 5'-ACA-CAACTGTGTTCA CTAGC-3' (Pco3) and SEQ ID NO:10: 5'-GTCTCCTTAAACCTGTCTTG-3' (GII) and the Taqman probe is SEQ ID NO:11: 5'-ACCTGACTCCTGAGG AGAAGTCT-3' that is HEX5'----3'TAMRA labeled. All patients will have persistence data and immune response data to the scFvFc: ζ and HyTK genes compared to determine if limited persistence can be attributed to the development of an immune response to gene-modified T cells.

Example 9

1. Staging Criteria and Patient Eligibility
a. Staging Criteria
Prior to Treatment
Immunohistopathologically confirmed recurrent/refractory neuroblastoma from tissue biopsy/marrow sample OR radiographic demonstration of tumor growth/recurrence at previous pathologically documented site of tumor.
CT Scan of Chest Abdomen and Pelvis with and without IV contrast.
MRI of Head with and without IV contrast.
Bone Scan and MIBG Scan (if available)
24-hour urine for HVA/VMA
Serum LDH and ferritin
Within 14 Days Prior to First T Cell Infusion
CT Scan of Chest Abdomen and Pelvis with and without IV contrast.

MRI of Head with and without IV contrast.
Bone Scan and MIBG Scan (if available providing that first scan was positive)
24-hour urine for HVA/VMA
Serum LDH and ferritin
b. Patient Eligibility
Patient Inclusion Criteria
Recurrent disseminated neuroblastoma or disseminated neuroblastoma that is refractory to $1^{st}$ line therapy.
Male or female subjects greater than 12 months of age.
Availability for peripheral blood sample drawing for study tests as outlined in Table 2.

responses are assessed by serial radiographic studies of areas of bulky disease, and/or bone marrow cytology in those subjects with marrow infiltration, and/or tumor markers (HVA, VMA).

3. Treatment Plan a. Schedule of Administration of $CE7R^+$, $CD8^+$ T Cell Clones A series of three escalating cell dose infusions (Table 3) can be administered to patients at two-week intervals. T cell infusions commence at the earliest time of their availability provided that recipients have recovered from the acute hematologic and toxic side effects of salvage chemotherapy.

TABLE 2

Calender of Specific Evaluations

| | Screening Visit | Infusion #1 | Day +1 | Day +7 | Infusion #2 Day +14 | Day +15 | Day +21 | Infusion #3 Day +28 | Day +29 | Day +35 | Day +42 | Day +56/70 | Day +100 |
|---|---|---|---|---|---|---|---|---|---|---|---|---|---|
| History and Physical/Lansky Score | X | X | X | X | X | X | X | X | X | X | X | X | X |
| CBC, DIFF, PLT | X | X | X | X | X | X | X | X | X | X | X | X | X |
| Chem 18 | X | X | X | X | X | X | X | X | X | X | X | X | X |
| EBV, HIV Serologies | X | | | | | | | | | | | | |
| Head CT* | X | | | | | | | | | | | | |
| PCR for plasmid Sequence in PBMC | | X | X | X | X | X | X | X | X | X | X | X | X |
| 24 Hr Urine for HVA/VMA | X | X* | | | | | | | | | X | | X |
| Radiographic/ BMA& BMX Disease Response | | X* | | | | | | | | | | X | X |
| Peripheral Blood for Immune Response | | | | | | | | | | | | | X |

*Studies are completed within 14 days prior to Infusion #1

2. Treatment Design and Rules for Dose Escalation

Peripheral blood mononuclear cells are obtained from patients by leukapheresis. Patient-derived T cell clones are generated from these leukapheresis products. Each participant receives a series of three escalating cell dose T cell infusions at two week intervals beginning as soon as clones are available and after recovery from all acute self-limited side effects of salvage chemotherapy. The salvage chemotherapy, administered by the patient's primary oncologist, is individualized to account for that child's previous treatment history, organ dysfunction, and disease sensitivity. The most common regimens are be cyclophosphamide/topotecan or ifosfamide/carboplatin/etoposide combinations, both of which have been extensively studied in children with recurrent solid tumors. The first cell dose is $10^8$ cells/m², the second $10^9$ cells/m², and the third $10^{10}$ cells/m². Recipients optionally can receive subcutaneously delivered low-dose rhIL-2 for ten days beginning 24-hrs following T cell adoptive transfer. Patients are evaluated prior to and weekly after the first infusion for a period of two months after which time, patients are evaluated monthly for an additional two months. Peripheral blood is drawn at specific times during the study to assay for the in vivo persistence of the transferred CTL clones and the induction of anti-scFvFc: ζ and HyTK immune responses. In those patients with detectable tumor at the time adoptive therapy commences, anti-tumor For those who do not meet the specified criteria (detailed below) for T cell re-infusion at the time clones are first available, T-cell clones are cryopreserved until these criteria are met. Clones are then thawed and undergo one two-week in vitro expansion cycle prior to re-infusion. The initial two cell doses are of modest numbers and consistent with cell doses used by Greenberg and Riddell [58]. Cell dose level III is higher than previously reported for T cell clones but within cell dose range of prior LAX cell studies. Low dose s.c. IL-2 is administered in a second cohort of five patients to support the in vivo persistence of transferred CTL. IL-2 injections begin 24-hrs following adoptive transfer of T cell clones and continue for ten days following the second and third T cell infusion provided no grade 3-4 toxicity is observed with the administration of the first T cell dose or is accompanied with the second T cell dose/IL-2.

TABLE 3

$CE7R^+HyTK^+$, $CD8^+$ Cytotoxic T Cell Administration Schedule

| Cell Dose | Protocol Day | Cohort 1 Cell Dose | Cohort 2 Cell Dose/IL-2 |
|---|---|---|---|
| I | 0 | 1 × 10⁸ cells/m² BSA | 1 × 10⁸ cells/m² BSA No IL-2 |

TABLE 3-continued

CE7R+HyTK+, CD8+ Cytotoxic T Cell Administration Schedule

| Cell Dose | Protocol Day | Cohort 1 Cell Dose | Cohort 2 Cell Dose/IL-2 |
|---|---|---|---|
| II | +14 | 1 × 10$^9$ cells/m$^2$ BSA | 1 × 10$^9$ cells/m$^2$ BSA s.c. IL-2 5 × 10$^5$ U/m$^2$ q12 hrs × 10 days |
| III | +28 | 1 × 10$^{10}$ cells/m$^2$ BSA | 1 × 10$^{10}$ cells/m$^2$ BSA s.c. IL-2 5 × 10$^5$ U/m$^2$ q12 hrs × 10 days |

Each infusion consists of a composite of up to five T cell clones to achieve the cell dose under study.

On the day of infusion T cell clones expanded in CRB-3008 are aseptically processed per standard technique on a CS-3000 blood separation device for cell washing and concentrating. Processed cells are resuspended in 100 ml of 0.9% NaCl with 2% human serum albumin in a bag suitable for clinical re-infusion.

Patients can be admitted to a hospital, for example, for their T cell infusions and are discharged no sooner than 23 hours following their infusion provided that no toxicities are observed. Otherwise patients remain hospitalized until resolution of any infusion-related toxicity deemed to pose a significant risk to the study subject as an outpatient.

T cells are infused intravenously over 30 minutes through a central line if available, if not an age appropriate sized I.V. catheter is inserted into a peripheral vein. The I.V tubing does not have a filter to avoid trapping of cells. The infusion bag is gently mixed every 5 minutes during the infusion.

The doctor or his representative is present during the infusion and immediately available for 2 hours following the infusion. Nursing observation and care is employed throughout the patient's hospital stay.

Subjects' oxygen saturation is measured by continuous pulse-oximetry beginning pre-infusion and continuing for at least 2 hrs or until readings return to their pre-infusion baseline.

Subjects experiencing regimen-related toxicities due to their salvage chemotherapy will have their infusion schedule delayed until these toxicities have resolved. The specific toxicities warranting delay of T cell infusions include: (a) Pulmonary: Requirement for supplemental oxygen to keep saturation greater than 95% or presence of radiographic abnormalities on chest x-ray that are progressive; (b) Cardiac: New cardiac arrhythmia not controlled with medical management. Hypotension requiring pressor support; (c) Active Infection: Positive blood cultures for bacteria, fungus, or virus within 48-hours of day 0; (d) Hepatic: Serum total bilirubin, or transaminases more than 5× normal limit; (e) Renal: Serum creatinine >2.0 or if patient requires dialysis; (f) Neurologic: Seizure activity within one week preceding day 0 or clinically detectable encephalopathy or new focal neurologic deficits; (g) Hematologic: Clinically evident bleeding diathesis or hemolysis. Platelet count must be greater than 20,000 and absolute neutrophil count greater than 500. Patients may be supported with PRBC and platelet transfusions.

b. Interleukin-2 Administration

Recombinant human IL-2 (rHuIL-2, Proleukin, Chiron, Emeryville, Calif.) resuspended for s.c. injection by standard pharmacy guidelines is administered provided that (1) no grade 3-4 oxicities are encountered in persons not receiving IL-2 at cell dose levels I-III and (2) no grade 3-4 toxicities are observed with the first and second cell doses in persons receiving IL-2. The initial IL-2 course is 5×10$^5$ U/m$^2$/dose q 12 hrs for 10 days beginning no sooner than 24-hrs following T cell re-infusion #2 and lasting no longer than 48-hrs prior to the third T cell dose (Day +28). A second IL-2 course of 5×10$^5$ U/m$^2$/dose q 12 hrs for 10 days is administered no sooner than 24-hrs following the third T cell dose provided no grade 3 or higher toxicity was encountered during the first IL-2 course. If grade 3-4 toxicity is encountered during the first IL-2 course, IL-2 is not administered following the third T cell dose. Patients not receiving IL-2 who have T cell persistence data (Q-PCR) demonstrating disappearance of clones following the third T cell infusion and those subjects receiving IL-2 who have completed the prescribed T cell infusions and IL-2 who similarly have persistence data demonstrating loss of clones in the circulation may receive further courses of IL-2 at the discretion of the treating physician.

c. Management of Toxicities and Complications

The management of mild transient symptoms such as have been observed with LAK, TIL, and T cell clone infusions symptoms is as follows. (1) All patients are pre-medicated with 15 mg/kg of acetaminophen p.o. (max. 650 mg.) and diphenhydramine 1 mg/kg I.V. (max dose 50 mg). (2) Fever, chills and temperature elevations >101° F. are managed with additional tylenol as clinically indicated, 10 mg/kg ibuprofen p.o. (max 400 mg) for breakthrough fevers, and 1 mg/kg demerol I.V. for chills (max 50 mg). Additional methods such as cooling blankets are employed for fevers resistant to these measures. All subjects that develop fever or chills have a blood culture drawn. Ceftriaxone 50 mg/kg I.V. (max dose 2 gms) is administered to non-allergic patients who in the opinion of the physician in attendance appear septic; alternate antibiotic choices are used as clinically indicated. (3) Headache is managed with acetaminophen. (4) Nausea and vomiting are treated with diphenhydramine 1 mg/kg I.V. (max 50 mg). (5) Transient hypotension is initially managed by intravenous fluid administration, however, patients with persistent hypotension require transfer to the intensive care unit for definitive medical treatment. (6) Hypoxemia is managed with supplemental oxygen.

Patients receive ganciclovir if grade 3 or 4 treatment-related toxicity is observed. Parentally administered ganciclovir is dosed at 10 mg/kg/day divided every 12 hours. A 14-day course is prescribed but may be extended should symptomatic resolution not be achieved in that time interval. All patients not hospitalized at the time of presenting symptoms are hospitalized for the first 72 hours of ganciclovir therapy for monitoring purposes. If symptoms do not respond to ganciclovir within 72 hours additional immunosuppressive agents including but not limited to corticosteroids and cyclosporin are added at the discretion of the treating physician.

d. Concomitant Therapy

All standard supportive care measures for patients undergoing therapies are used at the discretion of the patient's physician. Active infections are treated according to the standard of care.

4. Toxicities Monitored and Dosage Modifications a. Toxicities To Be Monitored

Toxicity criteria is per the NCI Common Toxicity Criteria (CTC) version 2.0 for toxicity and Adverse Event Reporting. A copy of the CTC version 2.0 is downloadable from the CTEP home page (http://ctep.info.nih.gov/1). All CTC guidelines apply to toxicity assessment except serum measurements of total bilirubin, ALT and AST as many cancer patients who have recently received chemotherapy frequently have prolonged elevations in bilirubin and hepatic transaminases. For those patients with elevated baseline serum levels of bilirubin, ALT or AST a grade 1 toxicity will be an elevation from their pre-T cell infusion baseline up to 2.5× that baseline level. Grade 2 hepatic will be a >2.5-5× rise from their pre-T cell infusion baseline, a grade 3 toxicity >5-20× rise, and grade 4>20× baseline. Any toxicity reported by research participants while receiving treatment or in follow-up for which there is no specific CTC designation will be graded on the following scale: Grade 0—no toxicity; Grade 1—mild toxicity, usually transient, requiring no special treatment and generally not interfering with usual daily activities; Grade 2—moderate toxicity that may be ameliorated by simple therapeutic maneuvers, and impairs usual activities; Grade 3—severe toxicity which requires therapeutic intervention and interrupts usual activities, hospitalization may be required or may not be required; Grade 4—life-threatening toxicity which requires hospitalization.

b. Criteria for Dose Modification

If a patient develops grade 2 toxicity with dose level I, the second cell dose for that patient remains at T cell dose level I. Only if the maximal toxicity observed with the second infusion is limited to grade 2 will the third and final cell dose be advanced to $10^9$ cells/m$^2$. For those persons requiring dose modification at cell infusion #2 who experience a grade 3 or greater toxicity with the second infusion, the third infusion is cancelled. If the first grade 2 toxicity occurs with the second cell dose, the third cell dose is held at dose level II.

c. Criteria for Removal of Patient from Treatment

If any patient develops grade 3 or higher toxicity, IL-2 if being administered, is stopped. Ganciclovir treatment as outlined above is initiated at the time a grade 3 or higher toxicity is encountered in those patients not receiving IL-2. For those patients receiving IL-2, ganciclovir treatment commences within 48-hours of stopping IL-2 if the encountered toxicity has not decreased to ≦grade 2 in that time interval. Grade 3 injection site toxicity is managed by discontinuation of IL-2 without T cell ablation with ganciclovir provided that this is the only Grade 3 or greater toxicity. Any patient requiring ganciclovir for T cell ablation do not receive further cell doses but continue being monitored per protocol. At the discretion of the treating physician, corticosteroids and/or other immunosuppressive drugs are added to ganciclovir should a more rapid tempo of resolution of severe toxicities be indicated.

d. Participant Premature Discontinuation

The reasons for premature discontinuation (for example, voluntary withdrawal, toxicity, death) are recorded on the case report form. Final study evaluations are completed at the time of discontinuation. Potential reasons for premature discontinuation include: (a) the development of a life-threatening infection; (b) the judgment of the treating physician that the patient is too ill to continue; (c) patient/family noncompliance with therapy and/or clinic appointments; (d) pregnancy; (e) voluntary withdrawal; (f) significant and rapid progression of neuroblastoma requiring alternative medical, radiation or surgical intervention; and (g) grade 3 or 4 toxicity judged to be possibly or probably related to study therapy.

5. Study Parameters and Calender (Table 2)

To occur concurrently with the patient's evaluation for disease relapse and prior to commencing with salvage chemotherapy. The specific studies/procedures include:

Review of pathologic specimens and/or radiographic studies to confirm diagnosis of recurrent/refractory neuroblastoma.

Verify inclusion/exclusion criteria by history.

Administer the educational proctoring to the potential research participant ($^3$7-yrs of age) and the parent/legal guardian, conduct the post-educational assessment.

Obtain informed consent.

Obtain EBV and HIV serologies.

Conduct staging studies as outlined above.

Obtain serum sample for HAMA analysis if patient has received prior murine monoclonal antibody therapy.

(b) Isolation of Peripheral Blood Mononuclear Cells for the Initiation of T Cell Cultures Patients satisfying inclusion criteria undergo a single leukapheresis procedure prior to receiving cytoreductive chemotherapy. The leukapheresis product is transferred to initiate T cell cultures.

(c) Day −14 to −1: Pre-T Cell Infusion Restaging

Conduct restaging studies as outlined above.

(d) Day 0: Evaluation Immediately Prior to T Cell Infusion

Review of medical status and review of systems

Physical examination, vital signs, weight, height, body surface area

List of concomitant medications and transfusions

Lansky performance status (see Table 4)

Complete blood count, differential, platelet count

Chem 18

Blood for protocol-specific studies (see Table 2)

TABLE 4

| | | Lansky Scale |
|---|---|---|
| | % | |
| Able to carry on normal activity; no special care needed | 100 | Fully active |
| | 90 | Minor restriction in physically strenuous play |
| | 80 | Restricted in strenuous play, tires more easily, otherwise active |
| Mild to moderate restriction | 70 | Both greater restrictions of, and less time spent in active play |
| | 60 | Ambulatory up to 50% of time, limited active play with assistance/supervision |
| | 50 | Considerable assistance required for any active play; fully able to engage in quiet play |
| Moderate to severe restriction | 40 | Able to initiate quiet activities |
| | 30 | Needs considerable assistance for quiet activity |
| | 20 | Limited to very passive activity initiated by others (e.g. TV) |
| | 10 | Completely disabled, not even passive play |

(e) Days 0, +14, +28: Clinical Evaluation During and after T Cell Infusions

Prior to the Infusion:

Interval History and Physical Exam

Blood draw for laboratory studies (see Table 2)

During the infusion:

Vital signs at time 0, and every 15 minutes during the infusion, continuous pulse oximetery Following the T cell infusion:

Vital Signs hourly for 12 hours

Oxygen saturation will be monitored for 2 hours following T cell infusions. Values will be recorded prior to initiating the infusion, immediately post-infusion, and 2 hours post-infusion. In addition, values will be recorded every 15 minutes if they fall below 90% until the patient recovers to his/her pre infusion room-air baseline saturation.

Events will be managed by standard medical practice.

Prior to Discharge:

Interval History and Physical Exam

Blood draw for laboratory studies (see Table 2)

(f) Days +1, +7, +15, +21, +29, +35, +42, +56, +70, +100

Interval History and Physical Exam

Blood draw for CBC, diff, plt, and Chem 18

3 cc/kg pt wt of heparinized (preservative-free heparin 10 U/10 ml) blood sent to CRB-3002 for direct assay of peripheral blood lymphocytes for vector DNA by PCR (g) Days −14-0, +42, +100

CT Scan of Sites of Recurrent Disease/MRI Head/Bone/MIBG Scans:

(h) Bone Marrow Aspirate and Biopsy: Days −14-0, +56, +100

(i) Days −1, +42, +100

24-hour urine collection for HVA, VMA (j) If a research participant is taken off treatment after receiving T cells, restaging bone marrow evaluation will be evaluated 28 days and 56 days following the last T cell dose administered.

6. Criteria for Evaluation and Endpoint Definitions (a) Criteria for Evaluation

The phase I data obtained at each clinical assessment is outlined in Table 2. The following toxicity and adverse event determination will be made: (a) symptoms and toxicities are evaluated as described above; (b) physical exam and blood chemistry/hematology results; and (c) adverse event reporting (b) Disease Status At each disease assessment outlined in Table 2 the determination of measurable disease is recorded as follows: (1) bidimensional measures of palpable disease and (2) on days +42 and +100 CT scans/MRI, bone scans, bone marrow studies, and Urine VMA/HVA determinations are evaluated and responses graded per the INSS Response Criteria (Table 5).

TABLE 5

INSS Response Criteria
Definition of Response to Treatment

| Response | Primary | Metastases | Markers |
|---|---|---|---|
| Complete Response (CR) | No tumor | No tumor (chest, abdomen, liver, bone, bone marrow, nodes, etc.) | HVA/VMA normal |
| Very Good Partial Response (VGPR) | Reduction >90% but <100% improved | No tumor (as above except bone); no new bone lesions, all pre-existing | HVA/VMA decreased >90% |
| Partial Response (PR) | Reduction 50-90% | No new lesions; 50-90% reduction in measurable sites; 0-1 bone marrow samples with tumor; bone lesions same as VGPR | HVA/VMA decreased 50-90% |
| Minor Response (MR) | | No new lesions; >50% reduction of any measurable lesion (primary or metastases) with <50% reduction in any other; or <25% increase in any existing lesion.# | |
| Stable disease (SD) | | No new lesions; <50% reduction but <25% increase in any existing lesion.# | |

TABLE 5-continued

INSS Response Criteria
Definition of Response to Treatment

| Response | Primary | Metastases | Markers |
|---|---|---|---|
| Progressive Disease (PD) | | Any new lesion; increase of any measurable lesion be >25%; previous negative marrow positive for tumor | |

Quantitative immunohistochemical assessment does not apply to marrow disease. Shrinkage in primary tumor or metastatic sites must last 4 weeks to be considered a response.

7. Reporting Adverse Events

Any sign, symptom or illness that appears to worsen during the study period regardless of the relationship to the study agent is an adverse event. All adverse events occurring during treatment, whether or not attributed to the agent, that are observed by the physician. Attributes include a description, onset and resolution date, duration, maximum severity, assessment of relationship to the treatment agent or other suspect agent(s), action taken and outcome. Toxicities are scored according to a 0-4 scale based on the criteria delineated in the Common Toxicity Criteria (CTC) Version 2.0 (see above). Association or relatedness to the treatment are graded as follows: 1=unrelated, 2=unlikely, 3=possibly, 4=probably, and 5=definitely related.

Unexpected adverse events are those which: (a) are not previously reported with adoptive T cell therapy and (b) are symptomatically and pathophysiologically related to a known toxicity but differ because of greater severity or specificity.

Appropriate clinical, diagnostic, and laboratory measures to attempt to delineate the cause of the adverse reaction in question must be performed and the results reported. All tests that reveal an abnormality considered to be related to adoptive transfer will be repeated at appropriate intervals until the course is determined or a return to normal values occurs.

8. Statistical Considerations

The type and grade of toxicities noted during therapy are summarized for each dose level. All adverse events noted by the investigator are tabulated according to the affected body system. Descriptive statistics are used to summarize the changes from baseline in clinical laboratory parameters. For those patients with measurable tumor at the time T cell therapy commences, responses are stratified per the INSS response criteria (Table 5) and summarized. Kaplan-Meier product limit methodology are used to estimate the survival. 95% confidence intervals are calculated for all described statistics.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Principles and Practice of Pediatric Oncology. third edition, edited by Philip A. Pizzo and David G. Poplack, Lippincott-Raven Publishers, Philadelphia, 1997.
2. Gurney, J. G. et al. Cancer 75:2186, 1995.
3. Coldman, A. J. et al. Cancer 46:1896, 1980.
4. Evans, A. E. et al. Cancer 59:1853, 1987.

5. Oppedal, B. R. et al. Cancer 62:772, 1988.
6. Castel, V. et al. Eur. J. Cancer 35:606, 1999.
7. Brodeur, G. M. et al. J. Clin. Oncol. 6:1874, 1988.
8. Brodeur, G. M. et al. J. Clin. Oncol. 11:1466, 1993.
9. Evans, A. E. et al. Prog. Clin. Biol. Res. 385:1994.
10. Green, A. A. et al. Cancer 48:2310, 1981.
11. Nitschke, R. et al. J. Clin. Oncol. 6:1271, 1988.
12. Matthay, K. K. et al. J. Clin. Oncol. 7:236,1989.
13. Castleberry, R. P. et al. J. Clin. Oncol. 10:1299, 1992.
14. Shafford, E. A. et al. J. Clin. Oncol. 2:742, 1984.
15. Castleberry, R. P. et al. J. Clin. Oncol. 9:789, 1991.
16. Matthay, K. K. et al. J. Clin. Oncol. 16:1256, 1998.
17. Paul, S. R. et al. Cancer 67:1493, 1991.
18. Matthay, K. K. et al. N. Engl. J. Med. 341:1165, 1999.
19. Bostrom, B. et al. Cancer Treat. Rep. 68:1157, 1984.
20. Pinkerton, C. R. et al. Med. Pediatr. Oncol. 15:236, 1987.
21. Hutchinson, R. J. et al. J. Nucl. Biol. Med. 35:237, 1991.
22. Ladenstein, R. et al. J. Clin. Oncol. 11:2330, 1993.
23. Kushner, B. H. et al. J. Clin. Oncol. 17:3221, 1999.
24. Schulz, G. et al. Cancer Res. 44:5914, 1984.
25. Wu, Z. L. et al. Cancer Res. 46:440, 1986.
26. Heiss, P. et al. Anticancer Res. 17:3145, 1997.
27. Cheung, N. K. et al. J. Clin. Oncol. 16:3053, 1998.
28. Kushner, B. H. et al. Blood 73:1936, 1989.
29. Hank, J. A. et al. Cancer Res. 50:5234, 1990.
30. Sondel, P. M. and Hank, J. A. Cancer J. Sci. Am. 3 Suppl 1:S121-7:S121, 1997.
31. Negrier, S. et al. J. Clin. Oncol. 9:1363, 1991 [Published Erratum Appears in J Clin Oncol 1992 June; 10(6):1026].
32. Pardo, N. et al. Med. Pediatr. Oncol. 27:534, 1996.
33. Pession, A. et al. Br. J. Cancer 78:528, 1998.
34. Murray, J. L. et al. J. Immunother. Emphasis. Tumor Immunol. 19:206, 1996.
35. Frost, J. D. et al. Cancer 80:317, 1997.
36. Gillies, S. D. et al. Proc. Natl. Acad. Sci. U.S.A. 89:1428, 1992.
37. Hank, J. A. et al. Clin. Cancer Res. 2:1951, 1996.
38. Benyunes, M. C. et al. Bone Marrow Transplant. 16:283, 1995.
39. Albertini, M. R. et al. Cancer 66:2457, 1990.
40. Katsanis, E. et al. Cancer Gene Ther. 2:39, 1995.
41. Heuer, J. G. et al. Hum. Gene Ther. 7:2059, 1996.
42. Bausero, M. A. et al. J. Immunother. Emphasis. Tumor Immunol. 19:113, 1996.
43. Hock, R. A. et al. Cancer Gene Ther. 3:314, 1996.
44. Lode, H. N. et al. Proc. Natl. Acad. Sci. U.S.A. 96:8591, 1999.
45. Yoshida, H. et al. Cancer Gene Ther. 6:395, 1999.
46. Roskrow, M. A. et al. Klin. Padiatr. 211:336, 1999.
47. Bowman, L. et al. Blood 92:1941, 1998.
48. Greenberg, P. D. Adv. Immunol. 49:281, 1991.
49. Enomoto, A. et al. Cancer Immunol. Immunother. 44:204, 1997.
50. Stevenson, P. G. et al. Eur. J. Immunol. 27:3259, 1997.
51. Schonmann, S. M. et al. Int. J. Cancer 37:255, 1986.
52. d'Uscio, C. H. et al. Br. J. Cancer 64:445, 1991.
53. d'Uscio, C. H. et al. J. Immunol. Methods 146:63, 1992.
54. Amstutz, H. et al. Int. J. Cancer 53:147, 1993.
55. Novak-Hofer, I. et al. J. Nucl. Med. 33:231, 1992.
56. Carrel, F. et al. Nucl. Med. Biol. 24:539, 1997.
57. Greenberg, P. D. Adv. Immunol., 49: 281-355, 1991.
58. Li, C. R. et al. Blood. 83(7): 1971-9, 1994.
59. Walter, E. A. et al. N Engl J Med. 333(16): 1038-44, 1995.
60. Heslop, H. E. et al. Immunol. Rev. 157:217, 1997.
61. Yee, C. et al. Curr. Opin. Immunol., 9: 702-708, 1997.
62. Greenberg, P. D. et al. Cancer J. Sci. Am. 4 Suppl 1:S100-5:S100, 1998.
63. Wilson, C. A. et al. Hum. Gene Ther. 8:869, 1997.
64. Smith, C. A. et al. J. Hematother. 4:73, 1995.
65. Riddell, S. R. et al. Nat. Med. 2:216, 1996.
66. Woffendin, C. et al. Proc. Natl. Acad. Sci. U.S.A. 93:2889, 1996.
67. Eshhar, Z. et al. Proc. Natl. Acad. Sci. U.S.A. 90:720, 1993.
68. Stancovski, I. et al. J. Immunol. 151:6577, 1993.
69. Darcy, P. K. et al. Eur. J. Immunol. 28:1663, 1998.
70. Moritz, D. et al. Proc. Natl. Acad. Sci. U.S.A. 91:4318, 1994.
71. Hekele, A. et al. Int. J. Cancer 68:232, 1996.
72. Bolhuis, R. L. et al. Adv. Exp. Med. Biol. 451:547-55: 547, 1998.
73. Altenschmidt, U. et al. J. Immunol. 159:5509, 1997.
74. Weijtens, M. E. et al. J. Immunol. 157:836, 1996.
75. Jensen, M. et al., Biol. Blood Marrow Transplant. 4:75, 1998.
76. Jensen, M. C. et al., Molecular Therapy 1(1):49-55, 2000.
77. Chu, G. et al. Nucleic. Acids. Res. 15:1311, 1987.
78. Gross et al., *Biochem. Soc. Trans.* 23:1079, 1995.
79. Hwu et al. *Cancer Res.* 55:3329, 1995.
80. Riddell et al., *Science* 257:238, 1992.
81. Heslop et al., *Nat. Med.* 2:551, 1996.
82. Rosenberg et al., *J. Natl. Cancer Inst* 85:622, 1993.
83. Rosenberg et al., *J. Natl. Cancer Inst* 85:1091, 1993.
84. Rosenberg et. al., *N. Engl. J. Med.* 319:1676, 1988.
85. Van Pel et al., *Immunol. Rev.* 145:229, 1995.
86. Irving et al., *Cell* 64:891, 1991.
87. Bird et al., *Science* 242:423, 1988.
88. Bird et al., *Science* 244(4903):409, 1989.
89. Bonini, C. et al. Science, 276: 1719-1724, 1997.
90. Roberts, et al. J. Immunol. 161(1):375-84, 1998.
91. Maniatis. T., et al. Molecular Cloning: A Laboratory Manual (Cold Spring Harbor Laboratory, Cold Spring Harbor, N.Y.) 1982.
92. Sambrook, J., et al. Molecular Cloning: A Laboratory Manual, 2nd Ed. (Cold Spring Harbor Laboratory, Cold Spring Harbor, N.Y.) 1989.
93. Ausubel, F. M., et al. Current Protocols in Molecular Biology, (J. Wiley and Sons, NY) 1992.
94. Glover, D. DNA Cloning, I and II (Oxford Press). 1985.
95. Anand, R. Techniques for the Analysis of Complex Genomes, (Academic Press) 1992.
96. Guthrie, G. and Fink, G. R. Guide to Yeast Genetics and Molecular Biology (Academic Press). 1991.
97. Harlow and Lane. Antibodies: A Laboratory Manual (Cold Spring Harbor Laboratory, Cold Spring Harbor, N.Y.) 1989.
98. Jakoby, W. B. and Pastan, I. H. (eds.) Cell Culture. Methods in Enzymology, Vol. 58 (Academic Press, Inc., Harcourt Brace Jovanovich (NY) 1979.
99. *Nucleic Acid Hybridization* (B. D. Hames & S. J. Higgins eds.) 1984.
100. *Transcription And Translation* (B. D. Hames & S. J. Higgins eds.) 1984.
101. *Culture Of Animal Cells* (R. I. Freshney, Alan R. Liss, Inc.) 1987.
102. *Immobilized Cells And Enzymes* (IRL Press) 1986.
103. B. Perbal, *A Practical Guide To Molecular Cloning* 1984.
104. *Methods In Enzymology* (Academic Press, Inc., N.Y.).

105. *Gene Transfer Vectors For Mammalian Cells* (J. H. Miller and M. P. Calos eds., Cold Spring Harbor Laboratory) 1987.
106. *Methods In Enzymology*, Vols. 154 and 155 (Wu et al. eds.), *Immunochemical Methods In Cell And Molecular Biology* (Mayer and Walker, eds., Academic Press, London) 1987.
107. *Handbook Of Experimental Immunology*, Volumes I-IV (D. M. Weir and C. C. Blackwell, eds.) 1986.
108. Hogan et al., Manipulating the Mouse Embryo, (Cold Spring Harbor Laboratory Press, Cold Spring Harbor, N.Y.) 1986.
109. Levitt et al., Genes Dev July; 3(7):1019-25, 1989.
110. Moreira et al., EMBO J. August 1; 14(15):3809-19 1995.
111. Goodwin and Rottman, J Biol. Chem. 1992 Aug. 15; 267(23):16330-4.

What is claimed is:

1. A CE7-specific chimeric T cell receptor comprising an intracellular signaling domain, a transmembrane domain and an extracellular domain, the extracellular domain comprising a CE7-specific receptor and wherein the CE7-specific chimeric T cell receptor comprises amino acids 21-631 of SEQ ID NO:2.

* * * * *

UNITED STATES PATENT AND TRADEMARK OFFICE
CERTIFICATE OF CORRECTION

PATENT NO. : 7,265,209 B2 Page 1 of 1
APPLICATION NO. : 11/477572
DATED : September 4, 2007
INVENTOR(S) : Michael Jensen It is certified that error appears in the above-identified patent and that said Letters Patent is hereby corrected as shown below:

In the Abstract

Page 1, line 10, "$F_c$" should be --Fc--

In the Specification

Col. 2, line 6, "that" should be --than--

Col. 5, line 40, "gancyclovir" should be --ganciclovir--

Col. 7, line 12, "$CD^+4CE7$" should be --$CD^+4$ CE7--

Col. 7, line 21, "CE7+" should be --$CE7^+$--

Col. 14, line 29 "CE7R+" should be --$CE7R^+$--

Col. 14, line 37, "Cytotolytic" should be --Cytolytic--

Col. 14, line 47, "$CE7R^+ CD8^+CTL$" should be --$CE7R$ $CD8^+$ CTL--

Col. 14, line 60, "$\zeta^+$" should be --$\zeta$--

Col. 15, line 33, "are" should be --and--

Col. 15, line 48, insert a period --.-- after "conditions"

Signed and Sealed this

Twentieth Day of November, 2007

JON W. DUDAS
*Director of the United States Patent and Trademark Office*

SEQUENCE LISTING

<160> NUMBER OF SEQ ID NOS: 11

<210> SEQ ID NO 1
<211> LENGTH: 1920
<212> TYPE: DNA
<213> ORGANISM: artificial sequence
<220> FEATURE:
<223> OTHER INFORMATION: mouse-human chimera
<220> FEATURE:
<221> NAME/KEY: CDS
<222> LOCATION: (14)..(1906)
<223> OTHER INFORMATION: scFvFc construct

<400> SEQUENCE: 1

```
cctcgagagc acc atg ctt ctc ctg gtg aca agc ctt ctg ctc tgt gag        49
            Met Leu Leu Leu Val Thr Ser Leu Leu Leu Cys Glu
              1               5                  10 tta cca cac cca gca ttc ctc ctg atc cca cag gtc caa ctg cag cag        97
Leu Pro His Pro Ala Phe Leu Leu Ile Pro Gln Val Gln Leu Gln Gln
         15                  20                  25 cct ggg gct gaa ctg gtg aag cct ggg gct tca gtg aag ctg tcc tgc       145
Pro Gly Ala Glu Leu Val Lys Pro Gly Ala Ser Val Lys Leu Ser Cys
     30                  35                  40 aag gct tct ggc tac acc ttc acc ggc tac tgg atg cac tgg gtg aag       193
Lys Ala Ser Gly Tyr Thr Phe Thr Gly Tyr Trp Met His Trp Val Lys
 45                  50                  55                  60 cag agg cct gga cat ggc ctt gag tgg att gga gag att aat cct agc       241
Gln Arg Pro Gly His Gly Leu Glu Trp Ile Gly Glu Ile Asn Pro Ser
                 65                  70                  75 aac ggt cgt act aac tac aat gag agg ttc aag agc aag gcc aca ctg       289
Asn Gly Arg Thr Asn Tyr Asn Glu Arg Phe Lys Ser Lys Ala Thr Leu
             80                  85                  90 act gta gac aaa tcc tcc acc aca gcc ttc atg caa ctc agc ggc ctg       337
Thr Val Asp Lys Ser Ser Thr Thr Ala Phe Met Gln Leu Ser Gly Leu
         95                 100                 105 aca tct gag gac tct gca gtc tat ttc tgt gca aga gat tac tac ggt       385
Thr Ser Glu Asp Ser Ala Val Tyr Phe Cys Ala Arg Asp Tyr Tyr Gly
     110                 115                 120 act agc tac aac ttt gac tac tgg ggc caa ggc acc act ctc aca gtc       433
Thr Ser Tyr Asn Phe Asp Tyr Trp Gly Gln Gly Thr Thr Leu Thr Val
 125                 130                 135                 140 tcc tca gga ggt ggc ggt agt gga ggt ggc gga tcc ggt ggc gga ggt       481
Ser Ser Gly Gly Gly Gly Ser Gly Gly Gly Gly Ser Gly Gly Gly Gly
                 145                 150                 155 agt gac atc cag atg aca caa tct tca tcc ttt tct gta tct cta           529
Ser Asp Ile Gln Met Thr Gln Ser Ser Ser Phe Ser Val Ser Leu
             160                 165                 170 gga gac aga gtc acc att act tgc aag gct aat gaa gac ata aat aat       577
Gly Asp Arg Val Thr Ile Thr Cys Lys Ala Asn Glu Asp Ile Asn Asn
         175                 180                 185 cgg tta gcc tgg tat cag cag aca cca gga aat tct cct agg ctc tta       625
```

-continued

```
                Arg Leu Ala Trp Tyr Gln Gln Thr Pro Gly Asn Ser Pro Arg Leu Leu
                    190                 195                 200 ata tct ggt gca acc aat ttg gta act ggg gtt cct tca aga ttc agt        673
Ile Ser Gly Ala Thr Asn Leu Val Thr Gly Val Pro Ser Arg Phe Ser
205                 210                 215                 220 ggc agt gga tct gga aag gat tac act ctc acc att acc agt ctt cag        721
Gly Ser Gly Ser Gly Lys Asp Tyr Thr Leu Thr Ile Thr Ser Leu Gln
                225                 230                 235 gct gaa gat ttt gct act tat tac tgt caa caa tat tgg agt act cca        769
Ala Glu Asp Phe Ala Thr Tyr Tyr Cys Gln Gln Tyr Trp Ser Thr Pro
            240                 245                 250 ttc acg ttc ggc tcg ggg aca gag ctc gag atc aaa gta gaa ccc aaa        817
Phe Thr Phe Gly Ser Gly Thr Glu Leu Glu Ile Lys Val Glu Pro Lys
        255                 260                 265 tct tct gac aaa act cac aca tgc cca ccg tgc cca gca cct gaa ctc        865
Ser Ser Asp Lys Thr His Thr Cys Pro Pro Cys Pro Ala Pro Glu Leu
    270                 275                 280 ctg ggg gga ccg tca gtc ttc ctc ttc ccc cca aaa ccc aag gac acc        913
Leu Gly Gly Pro Ser Val Phe Leu Phe Pro Pro Lys Pro Lys Asp Thr
285                 290                 295                 300 ctc atg atc tcc cgg acc cct gag gtc aca tgc gtg gtg gtg gac gtg        961
Leu Met Ile Ser Arg Thr Pro Glu Val Thr Cys Val Val Val Asp Val
                305                 310                 315 agc cac gaa gac cct gag gtc aag ttc aac tgg tac gtg gac ggc gtg       1009
Ser His Glu Asp Pro Glu Val Lys Phe Asn Trp Tyr Val Asp Gly Val
                320                 325                 330 gag gtg cat aat gcc aag aca aag ccg cgg gag gag cag tac aac agc       1057
Glu Val His Asn Ala Lys Thr Lys Pro Arg Glu Glu Gln Tyr Asn Ser
            335                 340                 345 acg tac cgt gtg gtc agc gtc ctc acc gtc ctg cac cag gac tgg ctg       1105
Thr Tyr Arg Val Val Ser Val Leu Thr Val Leu His Gln Asp Trp Leu
        350                 355                 360 aat ggc aag gag tac aag tgc aag gtc tcc aac aaa gcc ctc cca gcc       1153
Asn Gly Lys Glu Tyr Lys Cys Lys Val Ser Asn Lys Ala Leu Pro Ala
365                 370                 375                 380 ccc atc gag aaa acc atc tcc aaa gcc aaa ggg cag ccc cga gaa cca       1201
Pro Ile Glu Lys Thr Ile Ser Lys Ala Lys Gly Gln Pro Arg Glu Pro
                385                 390                 395 cag gtg tac acc ctg cca cca tca cga gat gag ctg acc aag aac cag       1249
Gln Val Tyr Thr Leu Pro Pro Ser Arg Asp Glu Leu Thr Lys Asn Gln
                400                 405                 410 gtc agc ctg acc tgc ctg gtc aaa ggc ttc tat ccc agc gac atc gcc       1297
Val Ser Leu Thr Cys Leu Val Lys Gly Phe Tyr Pro Ser Asp Ile Ala
            415                 420                 425 gtg gag tgg gag agc aat ggg cag ccg gag aac aac tac aag acc acg       1345
Val Glu Trp Glu Ser Asn Gly Gln Pro Glu Asn Asn Tyr Lys Thr Thr
        430                 435                 440 cct ccc gtg ctg gac tcc gac ggc tcc ttc ttc ctc tac agc aag ctc       1393
Pro Pro Val Leu Asp Ser Asp Gly Ser Phe Phe Leu Tyr Ser Lys Leu
445                 450                 455                 460 acc gtg gac aag agc agg tgg cag cag ggg aac gtc ttc tca tgc tcc       1441
Thr Val Asp Lys Ser Arg Trp Gln Gln Gly Asn Val Phe Ser Cys Ser
                465                 470                 475 gtg atg cat gag gct ctg cac aac cac tac acg cag aag agc ctc tcc       1489
Val Met His Glu Ala Leu His Asn His Tyr Thr Gln Lys Ser Leu Ser
            480                 485                 490 ctg tct ccc ggg aaa atg gcc ctg att gtg ctg ggg ggc gtc gcc ggc       1537
Leu Ser Pro Gly Lys Met Ala Leu Ile Val Leu Gly Gly Val Ala Gly
        495                 500                 505
```

-continued

```
ctc ctg ctt ttc att ggg cta ggc atc ttc ttc aga gtg aag ttc agc    1585
Leu Leu Leu Phe Ile Gly Leu Gly Ile Phe Phe Arg Val Lys Phe Ser
    510                 515                 520 agg agc gca gac gcc ccc gcg tac cag cag ggc cag aac cag ctc tat    1633
Arg Ser Ala Asp Ala Pro Ala Tyr Gln Gln Gly Gln Asn Gln Leu Tyr
525                 530                 535                 540 aac gag ctc aat cta gga cga aga gag gag tac gat gtt ttg gac aag    1681
Asn Glu Leu Asn Leu Gly Arg Arg Glu Glu Tyr Asp Val Leu Asp Lys
                545                 550                 555 aga cgt ggc cgg gac cct gag atg ggg gga aag ccg aga agg aag aac    1729
Arg Arg Gly Arg Asp Pro Glu Met Gly Gly Lys Pro Arg Arg Lys Asn
            560                 565                 570 cct cag gaa ggc ctg tac aat gaa ctg cag aaa gat aag atg gcg gag    1777
Pro Gln Glu Gly Leu Tyr Asn Glu Leu Gln Lys Asp Lys Met Ala Glu
        575                 580                 585 gcc tac agt gag att ggg atg aaa ggc gag cgc cgg agg ggc aag ggg    1825
Ala Tyr Ser Glu Ile Gly Met Lys Gly Glu Arg Arg Arg Gly Lys Gly
590                 595                 600 cac gat ggc ctt tac cag ggt ctc agt aca gcc acc aag gac acc tac    1873
His Asp Gly Leu Tyr Gln Gly Leu Ser Thr Ala Thr Lys Asp Thr Tyr
605                 610                 615                 620 gac gcc ctt cac atg cag gcc ctg ccc cct cgc taagcggccc ctag        1920
Asp Ala Leu His Met Gln Ala Leu Pro Pro Arg
                625                 630
```

<210> SEQ ID NO 2
<211> LENGTH: 631
<212> TYPE: PRT
<213> ORGANISM: artificial sequence
<220> FEATURE:
<223> OTHER INFORMATION: mouse-human chimera

<400> SEQUENCE: 2

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Pro Gly Ala Glu
            20                  25                  30

Leu Val Lys Pro Gly Ala Ser Val Lys Leu Ser Cys Lys Ala Ser Gly
        35                  40                  45

Tyr Thr Phe Thr Gly Tyr Trp Met His Trp Val Lys Gln Arg Pro Gly
    50                  55                  60

His Gly Leu Glu Trp Ile Gly Glu Ile Asn Pro Ser Asn Gly Arg Thr
65                  70                  75                  80

Asn Tyr Asn Glu Arg Phe Lys Ser Lys Ala Thr Leu Thr Val Asp Lys
                85                  90                  95

Ser Ser Thr Thr Ala Phe Met Gln Leu Ser Gly Leu Thr Ser Glu Asp
            100                 105                 110

Ser Ala Val Tyr Phe Cys Ala Arg Asp Tyr Tyr Gly Thr Ser Tyr Asn
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Phe Ser Val Ser Leu Gly Asp Arg Val
                165                 170                 175

Thr Ile Thr Cys Lys Ala Asn Glu Asp Ile Asn Asn Arg Leu Ala Trp
            180                 185                 190

Tyr Gln Gln Thr Pro Gly Asn Ser Pro Arg Leu Leu Ile Ser Gly Ala
```

-continued

```
            195                 200                 205
Thr Asn Leu Val Thr Gly Val Pro Ser Arg Phe Ser Gly Ser Gly Ser
        210                 215                 220
Gly Lys Asp Tyr Thr Leu Thr Ile Thr Ser Leu Gln Ala Glu Asp Phe
225                 230                 235                 240
Ala Thr Tyr Tyr Cys Gln Gln Tyr Trp Ser Thr Pro Phe Thr Phe Gly
                245                 250                 255
Ser Gly Thr Glu Leu Glu Ile Lys Val Glu Pro Lys Ser Ser Asp Lys
            260                 265                 270
Thr His Thr Cys Pro Pro Cys Pro Ala Pro Glu Leu Leu Gly Gly Pro
        275                 280                 285
Ser Val Phe Leu Phe Pro Pro Lys Pro Lys Asp Thr Leu Met Ile Ser
    290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
        355                 360                 365
Tyr Lys Cys Lys Val Ser Asn Lys Ala Leu Pro Ala Pro Ile Glu Lys
    370                 375                 380
Thr Ile Ser Lys Ala Lys Gly Gln Pro Arg Glu Pro Gln Val Tyr Thr
385                 390                 395                 400
Leu Pro Pro Ser Arg Asp Glu Leu Thr Lys Asn Gln Val Ser Leu Thr
                405                 410                 415
Cys Leu Val Lys Gly Phe Tyr Pro Ser Asp Ile Ala Val Glu Trp Glu
            420                 425                 430
Ser Asn Gly Gln Pro Glu Asn Asn Tyr Lys Thr Thr Pro Pro Val Leu
        435                 440                 445
Asp Ser Asp Gly Ser Phe Phe Leu Tyr Ser Lys Leu Thr Val Asp Lys
    450                 455                 460
Ser Arg Trp Gln Gln Gly Asn Val Phe Ser Cys Ser Val Met His Glu
465                 470                 475                 480
Ala Leu His Asn His Tyr Thr Gln Lys Ser Leu Ser Leu Ser Pro Gly
                485                 490                 495
Lys Met Ala Leu Ile Val Leu Gly Gly Val Ala Gly Leu Leu Leu Phe
            500                 505                 510
Ile Gly Leu Gly Ile Phe Phe Arg Val Lys Phe Ser Arg Ser Ala Asp
        515                 520                 525
Ala Pro Ala Tyr Gln Gln Gly Gln Asn Gln Leu Tyr Asn Glu Leu Asn
    530                 535                 540
Leu Gly Arg Arg Glu Glu Tyr Asp Val Leu Asp Lys Arg Arg Gly Arg
545                 550                 555                 560
Asp Pro Glu Met Gly Gly Lys Pro Arg Arg Lys Asn Pro Gln Glu Gly
                565                 570                 575
Leu Tyr Asn Glu Leu Gln Lys Asp Lys Met Ala Glu Ala Tyr Ser Glu
            580                 585                 590
Ile Gly Met Lys Gly Glu Arg Arg Arg Gly Lys Gly His Asp Gly Leu
        595                 600                 605
Tyr Gln Gly Leu Ser Thr Ala Thr Lys Asp Thr Tyr Asp Ala Leu His
    610                 615                 620
```

```
Met Gln Ala Leu Pro Pro Arg
625                 630

<210> SEQ ID NO 3
<211> LENGTH: 2100
<212> TYPE: DNA
<213> ORGANISM: Unknown
<220> FEATURE:
<223> OTHER INFORMATION: fragment of a modified pMG plasmid
<220> FEATURE:
<221> NAME/KEY: CDS
<222> LOCATION: (16)..(2088)
<223> OTHER INFORMATION: HyTK gene

<400> SEQUENCE: 3
ggtaggaggg ccatc atg aaa aag cct gaa ctc acc gcg acg tct gtc gcg        51
                Met Lys Lys Pro Glu Leu Thr Ala Thr Ser Val Ala
                  1               5                  10 aag ttt ctg atc gaa aag ttc gac agc gtc tcc gac ctg atg cag ctc         99
Lys Phe Leu Ile Glu Lys Phe Asp Ser Val Ser Asp Leu Met Gln Leu
         15                  20                  25 tcg gag ggc gaa gaa tct cgt gct ttc agc ttc gat gta gga ggg cgt        147
Ser Glu Gly Glu Glu Ser Arg Ala Phe Ser Phe Asp Val Gly Gly Arg
 30                  35                  40 gga tat gtc ctg cgg gta aat agc tgc gcc gat ggt ttc tac aaa gat        195
Gly Tyr Val Leu Arg Val Asn Ser Cys Ala Asp Gly Phe Tyr Lys Asp
 45                  50                  55                  60 cgt tat gtt tat cgg cac ttt gca tcg gcc gcg ctc ccg att ccg gaa        243
Arg Tyr Val Tyr Arg His Phe Ala Ser Ala Ala Leu Pro Ile Pro Glu
                 65                  70                  75 gtg ctt gac att ggg gaa ttc agc gag agc ctg acc tat tgc atc tcc        291
Val Leu Asp Ile Gly Glu Phe Ser Glu Ser Leu Thr Tyr Cys Ile Ser
         80                  85                  90 cgc cgt gca cag ggt gtc acg ttg caa gac ctg cct gaa acc gaa ctg        339
Arg Arg Ala Gln Gly Val Thr Leu Gln Asp Leu Pro Glu Thr Glu Leu
         95                 100                 105 ccc gct gtt ctg caa ccc gtc gcg gag ctc atg gat gcg atc gct gcg        387
Pro Ala Val Leu Gln Pro Val Ala Glu Leu Met Asp Ala Ile Ala Ala
    110                 115                 120 gcc gat ctt agc cag acg agc ggg ttc ggc cca ttc gga ccg caa gga        435
Ala Asp Leu Ser Gln Thr Ser Gly Phe Gly Pro Phe Gly Pro Gln Gly
125                 130                 135                 140 atc ggt caa tac act aca tgg cgt gat ttc ata tgc gcg att gct gat        483
Ile Gly Gln Tyr Thr Thr Trp Arg Asp Phe Ile Cys Ala Ile Ala Asp
                145                 150                 155 ccc cat gtg tat cac tgg caa act gtg atg gac gac acc gtc agt gcg        531
Pro His Val Tyr His Trp Gln Thr Val Met Asp Asp Thr Val Ser Ala
            160                 165                 170 tcc gtc gcg cag gct ctc gat gag ctg atg ctt tgg gcc gag gac tgc        579
Ser Val Ala Gln Ala Leu Asp Glu Leu Met Leu Trp Ala Glu Asp Cys
        175                 180                 185 ccc gaa gtc cgg cac ctc gtg cac gcg gat ttc ggc tcc aac aat gtc        627
Pro Glu Val Arg His Leu Val His Ala Asp Phe Gly Ser Asn Asn Val
    190                 195                 200 ctg acg gac aat ggc cgc ata aca gcg gtc att gac tgg agc gag gcg        675
Leu Thr Asp Asn Gly Arg Ile Thr Ala Val Ile Asp Trp Ser Glu Ala
205                 210                 215                 220 atg ttc ggg gat tcc caa tac gag gtc gcc aac atc ttc ttc tgg agg        723
Met Phe Gly Asp Ser Gln Tyr Glu Val Ala Asn Ile Phe Phe Trp Arg
                225                 230                 235 ccg tgg ttg gct tgt atg gag cag cag acg cgc tac ttc gag cgg agg        771
```

```
                Pro Trp Leu Ala Cys Met Glu Gln Gln Thr Arg Tyr Phe Glu Arg Arg
                                240                 245                 250 cat ccg gag ctt gca gga tcg ccg cgg ctc cgg gcg tat atg ctc cgc                819
His Pro Glu Leu Ala Gly Ser Pro Arg Leu Arg Ala Tyr Met Leu Arg
        255                 260                 265 att ggt ctt gac caa ctc tat cag agc ttg gtt gac ggc aat ttc gat                867
Ile Gly Leu Asp Gln Leu Tyr Gln Ser Leu Val Asp Gly Asn Phe Asp
    270                 275                 280 gat gca gct tgg gcg cag ggt cga tgc gac gca atc gtc cga tcc gga                915
Asp Ala Ala Trp Ala Gln Gly Arg Cys Asp Ala Ile Val Arg Ser Gly
285                 290                 295                 300 gcc ggg act gtc ggg cgt aca caa atc gcc cgc aga agc gcg gcc gtc                963
Ala Gly Thr Val Gly Arg Thr Gln Ile Ala Arg Arg Ser Ala Ala Val
                305                 310                 315 tgg acc gat ggc tgt gta gaa gtc gcg tct gcg ttc gac cag gct gcg               1011
Trp Thr Asp Gly Cys Val Glu Val Ala Ser Ala Phe Asp Gln Ala Ala
            320                 325                 330 cgt tct cgc ggc cat agc aac cga cgt acg gcg ttg cgc cct cgc cgg               1059
Arg Ser Arg Gly His Ser Asn Arg Arg Thr Ala Leu Arg Pro Arg Arg
        335                 340                 345 cag caa gaa gcc acg gaa gtc cgc ccg gag cag aaa atg ccc acg cta               1107
Gln Gln Glu Ala Thr Glu Val Arg Pro Glu Gln Lys Met Pro Thr Leu
    350                 355                 360 ctg cgg gtt tat ata gac ggt ccc cac ggg atg ggg aaa acc acc acc               1155
Leu Arg Val Tyr Ile Asp Gly Pro His Gly Met Gly Lys Thr Thr Thr
365                 370                 375                 380 acg caa ctg ctg gtg gcc ctg ggt tcg cgc gac gat atc gtc tac gta               1203
Thr Gln Leu Leu Val Ala Leu Gly Ser Arg Asp Asp Ile Val Tyr Val
                385                 390                 395 ccc gag ccg atg act tac tgg cgg gtg ctg ggg gct tcc gag aca atc               1251
Pro Glu Pro Met Thr Tyr Trp Arg Val Leu Gly Ala Ser Glu Thr Ile
            400                 405                 410 gcg aac atc tac acc aca caa cac cgc ctc gac cag ggt gag ata tcg               1299
Ala Asn Ile Tyr Thr Thr Gln His Arg Leu Asp Gln Gly Glu Ile Ser
        415                 420                 425 gcc ggg gac gcg gcg gtg gta atg aca agc gcc cag ata aca atg ggc               1347
Ala Gly Asp Ala Ala Val Val Met Thr Ser Ala Gln Ile Thr Met Gly
    430                 435                 440 atg cct tat gcc gtg acc gac gcc gtt ctg gct cct cat atc ggg ggg               1395
Met Pro Tyr Ala Val Thr Asp Ala Val Leu Ala Pro His Ile Gly Gly
445                 450                 455                 460 gag gct ggg agc tca cat gcc ccg ccc ccg gcc ctc acc ctc atc ttc               1443
Glu Ala Gly Ser Ser His Ala Pro Pro Pro Ala Leu Thr Leu Ile Phe
                465                 470                 475 gac cgc cat ccc atc gcc gcc ctc ctg tgc tac ccg gcc gcg cgg tac               1491
Asp Arg His Pro Ile Ala Ala Leu Leu Cys Tyr Pro Ala Ala Arg Tyr
            480                 485                 490 ctt atg ggc agc atg acc ccc cag gcc gtg ctg gcg ttc gtg gcc ctc               1539
Leu Met Gly Ser Met Thr Pro Gln Ala Val Leu Ala Phe Val Ala Leu
        495                 500                 505 atc ccg ccg acc ttg ccc ggc acc aac atc gtg ctt ggg gcc ctt ccg               1587
Ile Pro Pro Thr Leu Pro Gly Thr Asn Ile Val Leu Gly Ala Leu Pro
    510                 515                 520 gag gac aga cac atc gac cgc ctg gcc aaa cgc cag cgc ccc ggc gag               1635
Glu Asp Arg His Ile Asp Arg Leu Ala Lys Arg Gln Arg Pro Gly Glu
525                 530                 535                 540 cgg ctg gac ctg gct atg ctg gct gcg att cgc cgc gtt tac ggg cta               1683
Arg Leu Asp Leu Ala Met Leu Ala Ala Ile Arg Arg Val Tyr Gly Leu
                545                 550                 555
```

```
ctt gcc aat acg gtg cgg tat ctg cag tgc ggc ggg tcg tgg cgg gag    1731
Leu Ala Asn Thr Val Arg Tyr Leu Gln Cys Gly Gly Ser Trp Arg Glu
            560                 565                 570 gac tgg gga cag ctt tcg ggg acg gcc gtg ccg ccc cag ggt gcc gag    1779
Asp Trp Gly Gln Leu Ser Gly Thr Ala Val Pro Pro Gln Gly Ala Glu
        575                 580                 585 ccc cag agc aac gcg ggc cca cga ccc cat atc ggg gac acg tta ttt    1827
Pro Gln Ser Asn Ala Gly Pro Arg Pro His Ile Gly Asp Thr Leu Phe
    590                 595                 600 acc ctg ttt cgg gcc ccc gag ttg ctg gcc ccc aac ggc gac ctg tat    1875
Thr Leu Phe Arg Ala Pro Glu Leu Leu Ala Pro Asn Gly Asp Leu Tyr
605                 610                 615                 620 aac gtg ttt gcc tgg gcc ttg gac gtc ttg gcc aaa cgc ctc cgt tcc    1923
Asn Val Phe Ala Trp Ala Leu Asp Val Leu Ala Lys Arg Leu Arg Ser
                625                 630                 635 atg cac gtc ttt atc ctg gat tac gac caa tcg ccc gcc ggc tgc cgg    1971
Met His Val Phe Ile Leu Asp Tyr Asp Gln Ser Pro Ala Gly Cys Arg
            640                 645                 650 gac gcc ctg ctg caa ctt acc tcc ggg atg gtc cag acc cac gtc acc    2019
Asp Ala Leu Leu Gln Leu Thr Ser Gly Met Val Gln Thr His Val Thr
        655                 660                 665 acc ccc ggc tcc ata ccg acg ata tgc gac ctg gcg cgc acg ttt gcc    2067
Thr Pro Gly Ser Ile Pro Thr Ile Cys Asp Leu Ala Arg Thr Phe Ala
    670                 675                 680 cgg gag atg ggg gag gct aac tgagtcgaga at                          2100
Arg Glu Met Gly Glu Ala Asn
685                 690

<210> SEQ ID NO 4
<211> LENGTH: 691
<212> TYPE: PRT
<213> ORGANISM: Unknown
<220> FEATURE:
<223> OTHER INFORMATION: translation Product of SEQ ID NO:3

<400> SEQUENCE: 4

Met Lys Lys Pro Glu Leu Thr Ala Thr Ser Val Ala Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Leu Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175
```

```
Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
            195                 200                 205

Gly Arg Ile Thr Ala Val Ile Asp Trp Ser Glu Ala Met Phe Gly Asp
        210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
            275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Ala Ser Ala Phe Asp Gln Ala Ala Arg Ser Arg Gly
                325                 330                 335

His Ser Asn Arg Arg Thr Ala Leu Arg Pro Arg Gln Gln Glu Ala
            340                 345                 350

Thr Glu Val Arg Pro Glu Gln Lys Met Pro Thr Leu Leu Arg Val Tyr
            355                 360                 365

Ile Asp Gly Pro His Gly Met Gly Lys Thr Thr Thr Gln Leu Leu
        370                 375                 380

Val Ala Leu Gly Ser Arg Asp Asp Ile Val Tyr Val Pro Glu Pro Met
385                 390                 395                 400

Thr Tyr Trp Arg Val Leu Gly Ala Ser Glu Thr Ile Ala Asn Ile Tyr
                405                 410                 415

Thr Thr Gln His Arg Leu Asp Gln Gly Glu Ile Ser Ala Gly Asp Ala
            420                 425                 430

Ala Val Val Met Thr Ser Ala Gln Ile Thr Met Gly Met Pro Tyr Ala
            435                 440                 445

Val Thr Asp Ala Val Leu Ala Pro His Ile Gly Gly Glu Ala Gly Ser
        450                 455                 460

Ser His Ala Pro Pro Ala Leu Thr Leu Ile Phe Asp Arg His Pro
465                 470                 475                 480

Ile Ala Ala Leu Leu Cys Tyr Pro Ala Ala Arg Tyr Leu Met Gly Ser
                485                 490                 495

Met Thr Pro Gln Ala Val Leu Ala Phe Val Ala Leu Ile Pro Pro Thr
            500                 505                 510

Leu Pro Gly Thr Asn Ile Val Leu Gly Ala Leu Pro Glu Asp Arg His
            515                 520                 525

Ile Asp Arg Leu Ala Lys Arg Gln Arg Pro Gly Glu Arg Leu Asp Leu
        530                 535                 540

Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
                565                 570                 575

Leu Ser Gly Thr Ala Val Pro Pro Gln Gly Ala Glu Pro Gln Ser Asn
            580                 585                 590

Ala Gly Pro Arg Pro His Ile Gly Asp Thr Leu Phe Thr Leu Phe Arg
```

-continued

```
              595                 600                 605
Ala Pro Glu Leu Leu Ala Pro Asn Gly Asp Leu Tyr Asn Val Phe Ala
    610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
                645                 650                 655

Gln Leu Thr Ser Gly Met Val Gln Thr His Val Thr Thr Pro Gly Ser
            660                 665                 670

Ile Pro Thr Ile Cys Asp Leu Ala Arg Thr Phe Ala Arg Glu Met Gly
            675                 680                 685

Glu Ala Asn
    690
```

<210> SEQ ID NO 5
<211> LENGTH: 6834
<212> TYPE: DNA
<213> ORGANISM: artificial sequence
<220> FEATURE:
<223> OTHER INFORMATION: plasmid construct

<400> SEQUENCE: 5

| | | | | |
|---|---|---|---|---|
| tgttagcgaa | gaacatgtga | gcaaaaggcc | agcaaaaggc | caggaaccgt | aaaaaggccg | 60 |
| cgttgctggc | gtttttccat | aggctccgcc | cccctgacga | gcatcacaaa | aatcgacgct | 120 |
| caagtcagag | gtggcgaaac | ccgacaggac | tataaagata | ccaggcgttt | ccccctggaa | 180 |
| gctccctcgt | gcgctctcct | gttccgaccc | tgccgcttac | cggatacctg | tccgcctttc | 240 |
| tcccttcggg | aagcgtggcg | ctttctcata | gctcacgctg | taggtatctc | agttcggtgt | 300 |
| aggtcgttcg | ctccaagctg | ggctgtgtgc | acgaaccccc | cgttcagccc | gaccgctgcg | 360 |
| ccttatccgg | taactatcgt | cttgagtcca | acccggtaag | acacgactta | tcgccactgg | 420 |
| cagcagccac | tggtaacagg | attagcagag | cgaggtatgt | aggcggtgct | acagagttct | 480 |
| tgaagtggtg | gcctaactac | ggctacacta | gaagaacagt | atttggtatc | tgcgctctgc | 540 |
| tgaagccagt | taccttcgga | aaaagagttg | gtagctcttg | atccggcaaa | caaaccaccg | 600 |
| ctggtagcgg | tggttttttt | gtttgcaagc | agcagattac | gcgcagaaaa | aaaggatctc | 660 |
| aagaagatcc | tttgatcttt | tctacggggt | ctgacgctca | gtggaacgaa | aactcacgtt | 720 |
| aagggatttt | ggtcatggct | agttaattaa | gctgcaataa | acaatcatta | ttttcattgg | 780 |
| atctgtgtgt | tggttttttg | tgtgggcttg | ggggagggggg | aggccagaat | gactccaaga | 840 |
| gctacaggaa | ggcaggtcag | agaccccact | ggacaaacag | tggctggact | ctgcaccata | 900 |
| acacacaatc | aacaggggag | tgagctggat | cgagctagag | tctctagggc | cgcaataaaa | 960 |
| tatctttatt | ttcattacat | ctgtgtgttg | gttttttgtg | tgaatcgtaa | ctaacatacg | 1020 |
| ctctccatca | aaacaaaacg | aaacaaaaca | aactagcaaa | ataggctgtc | cccagtgcaa | 1080 |
| gtgcaggtgc | cagaacattt | ctctatcgaa | ggatctgcga | tcgctccggt | gcccgtcagt | 1140 |
| gggcagagcg | cacatcgccc | acagtccccg | agaagttggg | gggaggggtc | ggcaattgaa | 1200 |
| ccggtgccta | gagaaggtgg | cgcggggtaa | actgggaaag | tgatgtcgtg | tactggctcc | 1260 |
| gcctttttcc | cgagggtggg | ggagaaccgt | atataagtgc | agtagtcgcc | gtgaacgttc | 1320 |
| tttttcgcaa | cgggtttgcc | gccagaacac | agctgaagct | tcgaggggct | cgcatctctc | 1380 |
| cttcacgcgc | ccgccgccct | acctgaggcc | gccatccacg | ccggttgagt | cgcgttctgc | 1440 |
| cgcctcccgc | ctgtggtgcc | tcctgaactg | cgtccgccgt | ctaggtaagt | ttaaagctca | 1500 |

```
ggtcgagacc gggcctttgt ccggcgctcc cttggagcct acctagactc agccggctct    1560
ccacgctttg cctgaccctg cttgctcaac tctacgtctt tgtttcgttt tctgttctgc    1620
gccgttacag atccaagctg tgaccggcgc tacgtaagt gatatctact agatttatca     1680
aaaagagtgt tgacttgtga gcgctcacaa ttgatacgga ttcatcgaga gggacacgtc    1740
gactactaac cttcttctct ttcctacagc tgagatcacc ggcgaaggag gggcccccc     1800 tcgagagcac catgcttctc ctggtgacaa gccttctgct ctgtgagtta ccacacccag    1860
cattcctcct gatcccacag gtccaactgc agcagcctgg ggctgaactg gtgaagcctg    1920
gggcttcagt gaagctgtcc tgcaaggctt ctggctacac cttcaccggc tactggatgc    1980
actgggtgaa gcagaggcct ggacatggcc ttgagtggat tggagagatt aatcctagca    2040
acggtcgtac taactacaat gagaggttca agagcaaggc cacactgact gtagacaaat    2100
cctccaccac agccttcatg caactcagcg gcctgacatc tgaggactct gcagtctatt    2160
tctgtgcaag agattactac ggtactagct acaactttga ctactggggc caaggcacca    2220
ctctcacagt ctcctcagga ggtggcggta gtggaggtgg cggatccggt ggcggaggta    2280
gtgacatcca gatgacacaa tcttcatcct cctttctgt atctctagga gacagagtca     2340
ccattacttg caaggctaat gaagacataa ataatcggtt agcctggtat cagcagacac    2400
caggaaattc tcctaggctc ttaatatctg gtgcaaccaa tttggtaact ggggttcctt    2460
caagattcag tggcagtgga tctgaaaagg attacactct caccattacc agtcttcagg    2520
ctgaagattt tgctacttat tactgtcaac aatattggag tactccattc acgttcggct    2580
cggggacaga gctcgagatc aaagtagaac ccaaatcttc tgacaaaact cacacatgcc    2640
caccgtgccc agcacctgaa ctcctggggg gaccgtcagt cttcctcttc cccccaaaac    2700
ccaaggacac cctcatgatc tcccggaccc ctgaggtcac atgcgtggtg gtggacgtga    2760
gccacgaaga ccctgaggtc aagttcaact ggtacgtgga cggcgtggag gtgcataatg    2820
ccaagacaaa gccgcgggag gagcagtaca acagcacgta ccgtgtggtc agcgtcctca    2880
ccgtcctgca ccaggactgg ctgaatggca aggagtacaa gtgcaaggtc tccaacaaag    2940
ccctcccagc ccccatcgag aaaaccatct ccaaagccaa agggcagccc cgagaaccac    3000
aggtgtacac cctgccacca tcacgagatg agctgaccaa gaaccaggtc agcctgacct    3060
gcctggtcaa aggcttctat cccagcgaca tcgccgtgga gtgggagagc aatgggcagc    3120
cggagaacaa ctacaagacc acgcctcccg tgctggactc cgacggctcc ttcttcctct    3180
acagcaagct caccgtggac aagagcaggt ggcagcaggg gaacgtcttc tcatgctccg    3240
tgatgcatga ggctctgcac aaccactaca cgcagaagag cctctccctg tctccgggta    3300
aaatggccct gattgtgctg gggggcgtcg ccggcctcct gcttttcatt gggctaggca    3360
tcttcttcag agtgaagttc agcaggagcg cagacgcccc cgcgtaccag cagggccaga    3420
accagctcta taacgagctc aatctaggac gaagagagga gtacgatgtt ttggacaaga    3480
gacgtggccg ggaccctgag atgggggaa agccgagaag gaagaaccct caggaaggcc    3540
tgtacaatga actgcagaaa gataagatgg cggaggccta cagtgagatt gggatgaaag    3600
gcgagcgccg gaggggcaag gggcacgatg gcctttacca gggtctcagt acagccacca    3660
aggacaccta cgacgccctt cacatgcagg ccctgccccc tcgctaagcg gcccctagat    3720
cctagattga gtcgacgtta ctggccgaag ccgcttggaa taaggccggt gtgcgtttgt    3780
ctatatgtta ttttccacca tattgccgtc ttttggcaat gtgagggccc ggaaacctgg    3840
```

```
ccctgtcttc ttgacgagca ttcctagggg tctttcccct ctcgccaaag gaatgcaagg    3900
tctgttgaat gtcgtgaagg aagcagttcc tctggaagct tcttgaagac aaacaacgtc    3960
tgtagcgacc ctttgcaggc agcggaaccc cccacctggc gacaggtgcc tctgcggcca    4020
aaagccacgt gtataagata cacctgcaaa ggcggcacaa ccccagtgcc acgttgtgag    4080
ttggatagtt gtggaaagag tcaaatggct ctcctcaagc gtattcaaca agggctgaa     4140 ggatgcccag aaggtacccc attgtatggg atctgatctg gggcctcggt gcacatgctt    4200
tacatgtgtt tagtcgaggt taaaaaaacg tctaggcccc ccgaaccacg gggacgtggt    4260
tttcctttga aaaacacgat aataccatgg gtaagtgata tctactagtt gtgaccggcg    4320
cctagtgttg acaattaatc atcggcatag tatatcggca tagtataata cgactcacta    4380
taggagggcc accatgtcga ctactaacct tcttctcttt cctacagctg agatcaccgg    4440
taggagggcc atcatgaaaa agcctgaact caccgcgacg tctgtcgcga gtttctgat     4500 cgaaaagttc gacagcgtct ccgacctgat gcagctctcg gagggcgaag aatctcgtgc    4560
tttcagcttc gatgtaggag ggcgtggata tgtcctgcgg gtaaatagct gcgccgatgg    4620
tttctacaaa gatcgttatg tttatcggca ctttgcatcg gccgcgctcc cgattccgga    4680
agtgcttgac attggggaat tcagcgagag cctgacctat tgcatctccc gccgtgcaca    4740
gggtgtcacg ttgcaagacc tgcctgaaac cgaactgccc gctgttctgc aacccgtcgc    4800
ggagctcatg gatgcgatcg ctgcggccga tcttagccag acgagcgggt tcggcccatt    4860
cggaccgcaa ggaatcggtc aatacactac atggcgtgat ttcatatgcg cgattgctga    4920
tccccatgtg tatcactggc aaactgtgat ggacgacacc gtcagtgcgt ccgtcgcgca    4980
ggctctcgat gagctgatgc tttgggccga ggactgcccc gaagtccggc acctcgtgca    5040
cgcggatttc ggctccaaca atgtcctgac ggacaatggc cgcataacag cggtcattga    5100
ctggagcgag gcgatgttcg gggattccca atacgaggtc gccaacatct tcttctggag    5160
gccgtggttg gcttgtatgg agcagcagac gcgctacttc gagcggaggc atccggagct    5220
tgcaggatcg ccgcggctcc gggcgtatat gctccgcatt ggtcttgacc aactctatca    5280
gagcttggtt gacggcaatt tcgatgatgc agcttgggcg cagggtcgat gcgacgcaat    5340
cgtccgatcc ggagccggga ctgtcgggcg tacacaaatc gcccgcagaa gcgcggccgt    5400
ctggaccgat ggctgtgtag aagtcgcgtc tgcgttcgac caggctgcgc gttctcgcgg    5460
ccatagcaac cgacgtacgg cgttgcgccc tcgccggcag caagaagcca cggaagtccg    5520
cccggagcag aaaatgccca cgctactgcg ggtttatata gacggtcccc acgggatggg    5580
gaaaaccacc accacgcaac tgctggtggc cctgggttcg cgcgacgata tcgtctacgt    5640
acccgagccg atgacttact ggcgggtgct ggggcttcc gagacaatcg cgaacatcta    5700
caccacacaa caccgcctcg accagggtga gatatcggcc ggggacgcgg cggtggtaat    5760
gacaagcgcc cagataacaa tgggcatgcc ttatgccgtg accgacgccg ttctggctcc    5820
tcatatcggg gggaggctg ggagctcaca tgccccgccc ccggccctca ccctcatctt    5880
cgaccgccat cccatcgccg ccctcctgtg ctacccggcc gcgcggtacc ttatgggcag    5940
catgaccccc caggccgtgc tggcgttcgt ggccctcatc ccgccgacct tgcccggcac    6000
caacatcgtg cttggggccc ttccggagga cagacacatc gaccgcctgg ccaaacgcca    6060 gcgcccccggc gagcggctgg aacctggctat gctggctgcg attgccgcgg tttacgggct    6120
acttgccaat acggtgcggt atctgcagtg cggcgggtcg tggcgggagg actgggacca    6180
gctttcgggg acggccgtgc cgccccaggg tgccgagccc cagagcaacg cgggcccacg    6240
```

```
acccccatatc ggggacacgt tatttaccct gtttcgggcc cccgagttgc tggcccccaa    6300
cggcgacctg tataacgtgt ttgcctgggc cttggacgtc ttggccaaac gcctccgttc    6360
catgcacgtc tttatcctgg attacgacca atcgcccgcc ggctgccggg acgccctgct    6420
gcaacttacc tccgggatgg tccagaccca cgtcaccacc cccggctcca taccgacgat    6480
atgcgacctg gcgcgcacgt ttgcccggga gatgggggag gctaactgag tcgagaattc    6540
gctagagggc cctattctat agtgtcacct aaatgctaga gctcgctgat cagcctcgac    6600
tgtgccttct agttgccagc catctgttgt ttgcccctcc cccgtgcctt ccttgaccct    6660
ggaaggtgcc actcccactg tcctttccta ataaaatgag gaaattgcat cgcattgtct    6720
gagtaggtgt cattctattc tggggggtgg ggtggggcag gacagcaagg gggaggattg    6780
ggaagacaat agcaggcatg cgcagggccc aattgctcga gcgatctatc gaaa          6834

<210> SEQ ID NO 6
<211> LENGTH: 29
<212> TYPE: DNA
<213> ORGANISM: artificial sequence
<220> FEATURE:
<223> OTHER INFORMATION: synthetic oligonucleotide primer

<400> SEQUENCE: 6
tcttcctcta cacagcaagc tcaccgtgg                                        29

<210> SEQ ID NO 7
<211> LENGTH: 24
<212> TYPE: DNA
<213> ORGANISM: artificial sequence
<220> FEATURE:
<223> OTHER INFORMATION: synthetic oligonucleotide primer

<400> SEQUENCE: 7
gagggttctt ccttctcggc tttc                                             24

<210> SEQ ID NO 8
<211> LENGTH: 25
<212> TYPE: DNA
<213> ORGANISM: artificial sequence
<220> FEATURE:
<223> OTHER INFORMATION: synthetic oligonucleotide probe

<400> SEQUENCE: 8
ttcactctga agaagatgcc tagcc                                            25

<210> SEQ ID NO 9
<211> LENGTH: 20
<212> TYPE: DNA
<213> ORGANISM: artificial sequence
<220> FEATURE:
<223> OTHER INFORMATION: synthetic oligonucleotide primer

<400> SEQUENCE: 9
acacaactgt gttcactagc                                                  20

<210> SEQ ID NO 10
<211> LENGTH: 20
<212> TYPE: DNA
<213> ORGANISM: artificial sequence
<220> FEATURE:
<223> OTHER INFORMATION: synthetic oligonucleotide primer

<400> SEQUENCE: 10
```

```
gtctccttaa acctgtcttg                                              20

<210> SEQ ID NO 11
<211> LENGTH: 23
<212> TYPE: DNA
<213> ORGANISM: artificial sequence
<220> FEATURE:
<223> OTHER INFORMATION: synthetic oligonucleotide probe

<400> SEQUENCE: 11
acctgactcc tgaggagaag tct                                          23
```